United States Patent
Van Damme et al.

[11] Patent Number: 5,840,524
[45] Date of Patent: Nov. 24, 1998

[54] GRANULOCYTE CHEMOTACTIC PROTEIN

[75] Inventors: Jo Van Damme, Brussels; Paul Proost, Heverlee, both of Belgium

[73] Assignee: Stichting Rega vzw, Leuven, Belgium

[21] Appl. No.: 436,420

[22] PCT Filed: Nov. 26, 1993

[86] PCT No.: PCT/EP93/03330

§ 371 Date: May 24, 1995

§ 102(e) Date: May 24, 1995

[87] PCT Pub. No.: WO94/12537

PCT Pub. Date: Jun. 9, 1994

[51] Int. Cl.[6] .......................... C12P 21/06; A61K 38/00; C07H 21/04
[52] U.S. Cl. .................... 435/69.1; 530/300; 530/324; 536/23.1
[58] Field of Search .................... 435/69.1; 530/300, 530/324; 536/23.1

[56] References Cited

PUBLICATIONS

Walz, et al., Journal Exp. Med., vol. 174, Dec. 1991, pp. 1355–1362.
Goodman, et al., Journal Biol. Chem., vol. 266, No. 13, May 1991, pp. 8455–8463.
Goodman, et al., Biochemistry, vol. 31, No. 43, 1992, pp. 10483–10490.
Opdenakker, et al., Immunology Today, vol. 13, No. 11, 1992, pp. 463–464.
Rampart, et al., American Journal Pathology, vol. 135, No. 1, Jul. 1989, pp. 21–25.
Proost, et al., Biochemistry, vol. 32, No. 38, Sep. 1993, pp. 10170–10177.

*Primary Examiner*—Ponnathapura Achutamurthy
*Assistant Examiner*—Hankyel T. Park
*Attorney, Agent, or Firm*—Hale and Dorr LLP

[57] ABSTRACT

This invention is directed to a new family of mammalian chemokine proteins, which have been designated granulocyte chemotactic protein-2 (GCP-2) proteins, and includes mammalian GCP-2, sequence-related variants of mammalian GCP-2, and distinct peptide fragments of GCP-2.

20 Claims, 8 Drawing Sheets

| GCP-2 Protein | Amino Acid Sequence | SEQ ID NO |
|---|---|---|
| NH$_2$-terminal | GPVSAVLTELRCTCLRVTLRVNPKTIGKLQVFPAG(3) | 2 |
| | VSAVLTELRCTCLRVTLRVNPKTIGKLQVFPAG(3) | 3 |
| | VLTELRCTCLRVTLRVNPKTIGKLQVFPA(2) | 4 |
| | ELRCTCLRVTLRVNPKTIGKLQVFPAG(1) | 5 |
| Glu-C digest | VSAVLTELRXTXLRVTLRVN(1) VVASLKNGKQVCLDPE(3) | 6,7 |
| Lys-C digest | LQVFPAGPQCSK(1) QVCLDPEAPFLK(1) | 8,9 |
| | LQVFPAGPQCSKVEVVA(1) | 10 |
| | VEVVASLK(1) | 11 |
| Asp-N digest | ELRXTXLRVTLRVNPKTIGKLQVFPAGPQXSKVEVV(2) | 12 |
| HCOOH digest | PEAPFLKKVIQKILDSGNK(2) | 13 |

| Hu-GCP-2 | GPVSAVLTELRCTCLRVTLRVNPKTIGKLQVFPAGPQCSKVEVVASLKNGKQVCLDPEAPFLKKVIQKILDSGNK | 14 |
|---|---|---|
| | *** ** **** ** * *** ********** * **** ********* ** ******** | |
| Bo-GCP-2 | GPVAAVVRELRCVCLTTTPGIHPKTVSDLQVIAAGPQCSKVEVIATLKNGREVCLDPEAPLIKKIVQKILDSGKN | 15 |

| NH2-terminal | ELRXVXLTTTPGIHPKTVS(1) | 16 |
|---|---|---|
| | RELRCVCLTTTPGIHPKTVSDLQVIAAGPQCSKVEVIATLKNGRXV(1) | 17 |
| | VRELRCVCLTTTPGIHPKTVSDLQVIAAGPQ(2) | 18 |
| | GPVAAVVRELRXVXLTTTPGIHPKTVSDLQVIAAGPQ(1) | 19 |
| Arg-C digest | EVCLDPEAPLIK(1) | 20 |
| | IVQKILDSGKN(1) | 21 |
| | EVXLDPEAPLIK(1) | 22 |
| | KIVQKILDSGKN(1) | 23 |
| HCOOH digest | PEAPLIKKIVQKILDSGKN(1) | 24 |

| FRACTION (HPLC) | %ACETO-NITRILE | SEQUENCES DETECTED | SEQ ID NO |
|---|---|---|---|
| 54 | 29.5 | ELRCTCLRVTLR | 5 |
| 56 | 30 | VLTELRCTCLRVTLR | 4 |
| 60 | 31 | VSAVLTELRCTCLRVTLR | 3 |
| 67 | 32.5 | GPVSAVLTELRCTCLRV | 2 |

| CHEMOKINE | AMINO ACID SEQUENCE | SEQ ID NO |
|---|---|---|
| hu-IL-8 | EGAVLPRSAKELRCQCIKTYSKPFHPKFIKELRVIESGPHCANTEIIVKLSD GRELCLDPKENWVQRVVEKFLKRAENS | 25 |
| hu-GRO-α | ASVATELRCQCLQTLQG IHPKNIQSVNVKSPGPHCAQTEVIATLKN GRKACLNPASPIVKKIIEKMLNSDKSN | 26 |
| hu-GRO-β | APLATELRCQCLQTLQG IHLKNIQSVKVKSPGPHCAQTEVIATLKN GQKACLNPASPMVKKIIEKMLKNGKSN | 27 |
| hu-GRO-μ | ASVVTELRCQCLQTLQG IHLKNIQSVNVRSPGPHCAQTEVIATLKN GKKACLNPASPMVQKIIEKILNKGSTN | 28 |
| hu-IP-10 | VPLSRTVRCTCISISNQPVNPRSLEKLEIIPASQFCPRVEIIATMKKKGEKRCLNPESKAIKNLLKAVSKEMSKRSP | 29 |
| hu-PF-4 | EAEEDGDLQCLCVKTTSQ VRPRHITSLEVIKAGPHCPTAQLIATLKN GRKICLDLQAPLYKKIIKKLLES | 30 |
| hu-NAP-2 | AELRCMCIKTTSG IHPKNIQSLEVIGKGTHCNQVEVIATLKD GRKICLDPDAPRIKKIVQKKLAGDESAD | 31 |
| hu-ENA-78 | AGPAAAVLRELRCVCLQTTQG VHPKMISNLQVFAIGPQCSKVEVVASLKN GKEICLDPEAPFLKKVIQKILDGGNKEN | 32 |
| hu-GCP-2 | GPVSAVLTELRCTCLRVTLR VNPKTIGKLQVFPAGPQCSKVEVVASLKN GKQVCLDPEAPFLKKVIQKILDSGNK | 14 |
| hu-GCP-2 | GPVAAVVRELRCVCLTTTPG IHPKTVSDLQVIAAGPQCSKVEVIATLKN GREVCLDPEAPLIKKIVQKILDSGKN | 15 |
| bo-PF-4 | LSSFPATFVPI PADSEGGEDEDL QCVCLKTTSG INPRHISSLEVIGAGTHCPSPQIIATKKT GRKICLDQQRPLYKKILKLLDGDES | 33 |
| po-AMCF-I | DVLARVSAELRCQCINTHSTPFHPKFIKELRVIESGPHCENSEIIVKLVN GKEVCLDPKEKWVQKVVQIFLKRTEKQQQQQ | 34 |
| po-AMCF-II | SPIEAAEAAVVRELRCMCLTTTPG IHPKMISDLQVIPAGPQCSKAEVIATLKN GKEVCLDPKAPLIKKIVQKMLDSGKKKN | 35 |
| rab-IL-8 | AVLTRIGTELRCQCIKTHSTPFHPKFIKELRVIESGPHCANSEIIVKLVD GRELCLDPKEKWVQKVVQIFLKRAEQQES | 36 |
| rab-RPF2/GRO | ALTELRCQCLQTVQG IHLKSIQSLKVLSPGPHCAQT.... | 37 |
| ha-GRO | RLATGAPVANELRCQCLQTMTG VHLKNIESLKVTPPGPHCTQTEVIATLKN GQEACLNPEAPMVQKIVQKMLKSGIRK | 38 |
| rat-CINC/GRO | APVANELRCQCLQTVAG IHFKNIQSLKVMPPGPHCTQTEVIATLKN GREACLDPEAPMVQKIVQKMLKGVPK | 39 |
| rat-PF-4 | VTRASPEESDGDLSCVCVKTSSSRIHLKRITSLEVIKAGPHCAVPQLIATLKN GSKICLDRQVPLYKKIIKKLLES | 40 |
| mu-KC/GRO | RIATGAPIANELRCQCLQTMAG IHLKNIQSLKVLPSGPHCTQTFVIATLKN GRFACLDPEAPLVQKIVQKMLKGVPK | 41 |
| mu-MIP-2 | AVVASELRCQCLKTLPR VDFKNIQSLSVTPPGPHCAQTEVIATLKG GQKVCLDPEAPLVQKIIQKILNKGAN | 42 |
| mu-MIG/M119 | TLVIRNARCSCISTSRGTIHYKSLKDLKQFAPSPNCNKTEIIATLKN GDQTCLDPDSANVKKLMKEWEKKINQKKKQ...| 43 |
| mu-CRG-2 | IPLARTVRCNCIHIDDGPVRMRAIGKLEIIPASLSCPRVEIIATMKKNDEQRCLNPESKTIKNLMKAFSQKRSKRAP | 44 |
| ch-9E3 | RTLVKMGNELRCQCISTHSKFIHPKSIQDVKLTPSGPHCKNVEIIATLKD GREVCLDPTAPWVQLIVKALMAKAQLNSDAPL | 45 |

FIG. 8 ion, there is also provided a recombinant vector having incorporated therein a polynucleotide encoding a GCP-2 protein, and a host cell that has been engineered genetically to produce a GCP-2 protein having incorporated expressibly therein heterologous DNA encoding said GCP-2 protein.

SEQUENCE LISTING ( 1 ) GENERAL INFORMATION:

( i i i ) NUMBER OF SEQUENCES: 45

( 2 ) INFORMATION FOR SEQ ID NO: 1:

( i ) SEQUENCE CHARACTERISTICS:
        ( A ) LENGTH: 6 amino acids
        ( B ) TYPE: amino acid
        ( C ) STRANDEDNESS: double
        ( D ) TOPOLOGY: linear
            MOLECULE TYPE: peptide ( v ) FRAGMENT TYPE: internal ( i x ) FEATURE:
        ( A ) NAME/KEY: Modified-site (B) LOCATION: 4..6
(D) OTHER INFORMATION: /note= "Xaa represents any amino acid"

(xi) SEQUENCE DESCRIPTION: SEQ ID NO: 1:

Glu Leu Arg Cys Xaa Cys
1               5

(2) INFORMATION FOR SEQ ID NO: 2:

(i) SEQUENCE CHARACTERISTICS:
(A) LENGTH: 35 amino acids
(B) TYPE: amino acid
(D) TOPOLOGY: linear (ii) MOLECULE TYPE: protein (v) FRAGMENT TYPE: N-terminal (xi) SEQUENCE DESCRIPTION: SEQ ID NO: 2:

Gly Pro Val Ser Ala Val Leu Thr Glu Leu Arg Cys Thr Cys Leu Arg
1               5                   10                  15
Val Thr Leu Arg Val Asn Pro Lys Thr Ile Gly Lys Leu Gln Val Phe
                20                  25                  30
Pro Ala Gly
        35

(2) INFORMATION FOR SEQ ID NO: 3:

(i) SEQUENCE CHARACTERISTICS:
(A) LENGTH: 33 amino acids
(B) TYPE: amino acid
(D) TOPOLOGY: linear (ii) MOLECULE TYPE: protein (v) FRAGMENT TYPE: N-terminal (xi) SEQUENCE DESCRIPTION: SEQ ID NO: 3:

Val Ser Ala Val Leu Thr Glu Leu Arg Cys Thr Cys Leu Arg Val Thr
1               5                   10                  15
Leu Arg Val Asn Pro Lys Thr Ile Gly Lys Leu Gln Val Phe Pro Ala
                20                  25                  30
Gly (2) INFORMATION FOR SEQ ID NO: 4:

(i) SEQUENCE CHARACTERISTICS:
(A) LENGTH: 29 amino acids
(B) TYPE: amino acid
(D) TOPOLOGY: linear (ii) MOLECULE TYPE: protein (v) FRAGMENT TYPE: N-terminal (xi) SEQUENCE DESCRIPTION: SEQ ID NO: 4:

Val Leu Thr Glu Leu Arg Cys Thr Cys Leu Arg Val Thr Leu Arg Val
1               5                   10                  15
Asn Pro Lys Thr Ile Gly Lys Leu Gln Val Phe Pro Ala
                20                  25

(2) INFORMATION FOR SEQ ID NO: 5:

(i) SEQUENCE CHARACTERISTICS:
(A) LENGTH: 27 amino acids
(B) TYPE: amino acid (D) TOPOLOGY: linear (i i) MOLECULE TYPE: protein (v) FRAGMENT TYPE: N-terminal (x i) SEQUENCE DESCRIPTION: SEQ ID NO: 5:

```
Glu  Leu  Arg  Cys  Thr  Cys  Leu  Arg  Val  Thr  Leu  Arg  Val  Asn  Pro  Lys
1                  5                       10                      15
Thr  Ile  Gly  Lys  Leu  Gln  Val  Phe  Pro  Ala  Gly
                20                      25
```

(2) INFORMATION FOR SEQ ID NO: 6:

(i) SEQUENCE CHARACTERISTICS:
        (A) LENGTH: 20 amino acids
        (B) TYPE: amino acid
        (D) TOPOLOGY: linear (i i) MOLECULE TYPE: peptide (v) FRAGMENT TYPE: N-terminal (i x) FEATURE:
        (A) NAME/KEY: Modified-site
        (B) LOCATION: 10..12
        (D) OTHER INFORMATION: /note= "Xaa was ambiguous or
            undetectable at time of determination; later
            identified as "Cys""

(x i) SEQUENCE DESCRIPTION: SEQ ID NO: 6:

```
Val  Ser  Ala  Val  Leu  Thr  Glu  Leu  Arg  Xaa  Thr  Xaa  Leu  Arg  Val  Thr
1                  5                       10                      15
Leu  Arg  Val  Asn
                20
```

(2) INFORMATION FOR SEQ ID NO: 7:

(i) SEQUENCE CHARACTERISTICS:
        (A) LENGTH: 16 amino acids
        (B) TYPE: amino acid
        (D) TOPOLOGY: linear (i i) MOLECULE TYPE: peptide (v) FRAGMENT TYPE: internal (x i) SEQUENCE DESCRIPTION: SEQ ID NO: 7:

```
Val  Val  Ala  Ser  Leu  Lys  Asn  Gly  Lys  Gln  Val  Cys  Leu  Asp  Pro  Glu
1                  5                       10                      15
```

(2) INFORMATION FOR SEQ ID NO: 8:

(i) SEQUENCE CHARACTERISTICS:
        (A) LENGTH: 12 amino acids
        (B) TYPE: amino acid
        (D) TOPOLOGY: linear (i i) MOLECULE TYPE: peptide (v) FRAGMENT TYPE: internal (x i) SEQUENCE DESCRIPTION: SEQ ID NO: 8:

```
Leu  Gln  Val  Phe  Pro  Ala  Gly  Pro  Gln  Cys  Ser  Lys
1                  5                       10
```

(2) INFORMATION FOR SEQ ID NO: 9:

(i) SEQUENCE CHARACTERISTICS:
        (A) LENGTH: 12 amino acids (B) TYPE: amino acid
(D) TOPOLOGY: linear (ii) MOLECULE TYPE: peptide (v) FRAGMENT TYPE: internal (xi) SEQUENCE DESCRIPTION: SEQ ID NO: 9:

```
Gln  Val  Cys  Leu  Asp  Pro  Glu  Ala  Pro  Phe  Leu  Lys
 1              5                        10
```

(2) INFORMATION FOR SEQ ID NO: 10:

(i) SEQUENCE CHARACTERISTICS:
    (A) LENGTH: 17 amino acids
    (B) TYPE: amino acid
    (D) TOPOLOGY: linear (ii) MOLECULE TYPE: peptide (v) FRAGMENT TYPE: internal (xi) SEQUENCE DESCRIPTION: SEQ ID NO: 10:

```
Leu  Gln  Val  Phe  Pro  Ala  Gly  Pro  Gln  Cys  Ser  Lys  Val  Glu  Val  Val
 1              5                        10                       15
Ala
```

(2) INFORMATION FOR SEQ ID NO: 11:

(i) SEQUENCE CHARACTERISTICS:
    (A) LENGTH: 8 amino acids
    (B) TYPE: amino acid
    (D) TOPOLOGY: linear (ii) MOLECULE TYPE: peptide (v) FRAGMENT TYPE: internal (xi) SEQUENCE DESCRIPTION: SEQ ID NO: 11:

```
Val  Glu  Val  Val  Ala  Ser  Leu  Lys
 1              5
```

(2) INFORMATION FOR SEQ ID NO: 12:

(i) SEQUENCE CHARACTERISTICS:
    (A) LENGTH: 36 amino acids
    (B) TYPE: amino acid
    (D) TOPOLOGY: linear (ii) MOLECULE TYPE: peptide (v) FRAGMENT TYPE: internal (ix) FEATURE:
    (A) NAME/KEY: Modified-site
    (B) LOCATION: 4..6
    (D) OTHER INFORMATION: /label=xtx
        / note= "x was ambiguous at time of determination"

(ix) FEATURE:
    (A) NAME/KEY: Modified-site
    (B) LOCATION: 29..31
    (D) OTHER INFORMATION: /label=qxs
        / note= "x was ambiguous at time of determination;
        later identified as "c""

(xi) SEQUENCE DESCRIPTION: SEQ ID NO: 12:

```
Glu  Leu  Arg  Xaa  Thr  Xaa  Leu  Arg  Val  Thr  Leu  Arg  Val  Asn  Pro  Lys
 1              5                        10                       15
Thr  Ile  Gly  Lys  Leu  Gln  Val  Phe  Pro  Ala  Gly  Pro  Gln  Xaa  Ser  Lys
             20                       25                       30
```

```
            Val   Glu   Val   Val
                   35
```

( 2 ) INFORMATION FOR SEQ ID NO: 13:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( v ) FRAGMENT TYPE: C-terminal ( x i ) SEQUENCE DESCRIPTION: SEQ ID NO: 13:

```
Pro   Glu   Ala   Pro   Phe   Leu   Lys   Lys   Val   Ile   Gln   Lys   Ile   Leu   Asp   Ser
 1                       5                            10                            15
Gly   Asn   Lys
```

( 2 ) INFORMATION FOR SEQ ID NO: 14:

( i ) SEQUENCE CHARACTERISTICS:
        ( A ) LENGTH: 75 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 14:

```
Gly   Pro   Val   Ser   Ala   Val   Leu   Thr   Glu   Leu   Arg   Cys   Thr   Cys   Leu   Arg
 1                       5                            10                            15
Val   Thr   Leu   Arg   Val   Asn   Pro   Lys   Thr   Ile   Gly   Lys   Leu   Gln   Val   Phe
                  20                          25                            30
Pro   Ala   Gly   Pro   Gln   Cys   Ser   Lys   Val   Glu   Val   Val   Ala   Ser   Leu   Lys
                  35                          40                            45
Asn   Gly   Lys   Gln   Val   Cys   Leu   Asp   Pro   Glu   Ala   Pro   Phe   Leu   Lys   Lys
                  50                          55                            60
Val   Ile   Gln   Lys   Ile   Leu   Asp   Ser   Gly   Asn   Lys
 65                          70                           75
```

( 2 ) INFORMATION FOR SEQ ID NO: 15:

( i ) SEQUENCE CHARACTERISTICS:
        ( A ) LENGTH: 75 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 15:

```
Gly   Pro   Val   Ala   Ala   Val   Val   Arg   Glu   Leu   Arg   Cys   Val   Cys   Leu   Thr
 1                       5                            10                            15
Thr   Thr   Pro   Gly   Ile   His   Pro   Lys   Thr   Val   Ser   Asp   Leu   Gln   Val   Ile
                  20                          25                            30
Ala   Ala   Gly   Pro   Gln   Cys   Ser   Lys   Val   Glu   Val   Ile   Ala   Thr   Leu   Lys
                  35                          40                            45
Asn   Gly   Arg   Glu   Val   Cys   Leu   Asp   Pro   Glu   Ala   Pro   Leu   Ile   Lys   Lys
                  50                          55                            60
Ile   Val   Gln   Lys   Ile   Leu   Asp   Ser   Gly   Lys   Asn
 65                          70                           75
```

( 2 ) INFORMATION FOR SEQ ID NO: 16:

( i ) SEQUENCE CHARACTERISTICS:
    ( A ) LENGTH: 19 amino acids
    ( B ) TYPE: amino acid
    ( D ) TOPOLOGY: linear ( i i ) MOLECULE TYPE: peptide ( v ) FRAGMENT TYPE: N-terminal ( i x ) FEATURE:
    ( A ) NAME/KEY: Modified-site
    ( B ) LOCATION: 4..6
    ( D ) OTHER INFORMATION: /note= "Xaa was ambiguous at time
         of determination; later identified as "C...""

( x i ) SEQUENCE DESCRIPTION: SEQ ID NO: 16:

```
Glu  Leu  Arg  Xaa  Val  Xaa  Leu  Thr  Thr  Thr  Pro  Gly  Ile  His  Pro  Lys
1                  5                             10                           15

Thr  Val  Ser
```

( 2 ) INFORMATION FOR SEQ ID NO: 17:

( i ) SEQUENCE CHARACTERISTICS:
    ( A ) LENGTH: 46 amino acids
    ( B ) TYPE: amino acid
    ( D ) TOPOLOGY: linear ( i i ) MOLECULE TYPE: peptide ( v ) FRAGMENT TYPE: N-terminal ( i x ) FEATURE:
    ( A ) NAME/KEY: Modified-site
    ( B ) LOCATION: 44..46
    ( D ) OTHER INFORMATION: /note= "Xaa was ambiguous at time
         of determination; later identified as "G...""

( x i ) SEQUENCE DESCRIPTION: SEQ ID NO: 17:

```
Arg  Glu  Leu  Arg  Cys  Val  Cys  Leu  Thr  Thr  Thr  Pro  Gly  Ile  His  Pro
1                  5                             10                           15

Lys  Thr  Val  Ser  Asp  Leu  Gln  Val  Ile  Ala  Ala  Gly  Pro  Gln  Cys  Ser
                    20                        25                      30

Lys  Val  Glu  Val  Ile  Ala  Thr  Leu  Lys  Asn  Gly  Arg  Xaa  Val
               35                        40                      45
```

( 2 ) INFORMATION FOR SEQ ID NO: 18:

( i ) SEQUENCE CHARACTERISTICS:
    ( A ) LENGTH: 31 amino acids
    ( B ) TYPE: amino acid
    ( D ) TOPOLOGY: linear ( i i ) MOLECULE TYPE: peptide ( v ) FRAGMENT TYPE: N-terminal ( i x ) FEATURE:
    ( A ) NAME/KEY: Modified-site
    ( B ) LOCATION: 12..14
    ( D ) OTHER INFORMATION: /note= "Xaa was ambiguous at time
         of determination; later identified as "C...""

( x i ) SEQUENCE DESCRIPTION: SEQ ID NO: 18:

```
Val  Arg  Glu  Leu  Arg  Xaa  Val  Xaa  Leu  Thr  Thr  Thr  Pro  Gly  Ile  His
1                  5                             10                           15

Pro  Lys  Thr  Val  Ser  Asp  Leu  Gln  Val  Ile  Ala  Ala  Gly  Pro  Gln
                    20                        25                      30
```

( 2 ) INFORMATION FOR SEQ ID NO: 19:

( i ) SEQUENCE CHARACTERISTICS:
    ( A ) LENGTH: 37 amino acids
    ( B ) TYPE: amino acid
    ( D ) TOPOLOGY: linear ( i i ) MOLECULE TYPE: peptide ( v ) FRAGMENT TYPE: N-terminal ( i x ) FEATURE:
    ( A ) NAME/KEY: Modified-site
    ( B ) LOCATION: 12..14
    ( D ) OTHER INFORMATION: /note= "Xaa was ambiguous at time
        of determination; later identified as "C..."

( x i ) SEQUENCE DESCRIPTION: SEQ ID NO: 19:

Gly Pro Val Ala Ala Val Val Arg Glu Leu Arg Xaa Val Xaa Leu Thr
1               5                   10                  15

Thr Thr Pro Gly Ile His Pro Lys Thr Val Ser Asp Leu Gln Val Ile
            20              25                  30

Ala Ala Gly Pro Gln
            35

( 2 ) INFORMATION FOR SEQ ID NO: 20:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO: 20:

Glu Val Cys Leu Asp Pro Glu Ala Pro Leu Ile Lys
1               5                   10

( 2 ) INFORMATION FOR SEQ ID NO: 21:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: peptide ( v ) FRAGMENT TYPE: C-terminal ( x i ) SEQUENCE DESCRIPTION: SEQ ID NO: 21:

Ile Val Gln Lys Ile Leu Asp Ser Gly Lys Asn
1               5                   10

( 2 ) INFORMATION FOR SEQ ID NO: 22:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( v ) FRAGMENT TYPE: internal ( i x ) FEATURE:
    ( A ) NAME/KEY: Modified-site
    ( B ) LOCATION: 2..4
    ( D ) OTHER INFORMATION: /note= "Xaa was ambiguous at time
        of determination; later identified as "C..."

( x i ) SEQUENCE DESCRIPTION: SEQ ID NO: 22:

Glu Val Xaa Leu Asp Pro Glu Ala Pro Leu Ile Lys
1               5                   10

(2) INFORMATION FOR SEQ ID NO: 23:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (v) FRAGMENT TYPE: C-terminal (xi) SEQUENCE DESCRIPTION: SEQ ID NO: 23:

Lys Ile Val Gln Lys Ile Leu Asp Ser Gly Lys Asn
1               5                   10

(2) INFORMATION FOR SEQ ID NO: 24:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: C-terminal (xi) SEQUENCE DESCRIPTION: SEQ ID NO: 24:

Pro Glu Ala Pro Leu Ile Lys Lys Ile Val Gln Lys Ile Leu Asp Ser
1               5                   10                  15

Gly Lys Asn (2) INFORMATION FOR SEQ ID NO: 25:

(i) SEQUENCE CHARACTERISTICS:
        (A) LENGTH: 79 amino acids
        (B) TYPE: amino acid
        (D) TOPOLOGY: linear (ii) MOLECULE TYPE: protein (xi) SEQUENCE DESCRIPTION: SEQ ID NO: 25:

Glu Gly Ala Val Leu Pro Arg Ser Ala Lys Glu Leu Arg Cys Gln Cys
1               5                   10                  15

Ile Lys Thr Tyr Ser Lys Pro Phe His Pro Lys Phe Ile Lys Glu Leu
                20                  25                  30

Arg Val Ile Glu Ser Gly Pro His Cys Ala Asn Thr Glu Ile Ile Val
                35                  40                  45

Lys Leu Ser Asp Gly Arg Glu Leu Cys Leu Asp Pro Lys Glu Asn Trp
        50                  55                  60

Val Gln Arg Val Val Glu Lys Phe Leu Lys Arg Ala Glu Asn Ser
65                  70                  75

(2) INFORMATION FOR SEQ ID NO: 26:

(i) SEQUENCE CHARACTERISTICS:
        (A) LENGTH: 73 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 26:

Ala Ser Val Ala Thr Glu Leu Arg Cys Gln Cys Leu Gln Thr Leu Gln
1               5                   10                  15

Gly Ile His Pro Lys Asn Ile Gln Ser Val Asn Val Lys Ser Pro Gly
            20              25                  30

Pro His Cys Ala Gln Thr Glu Val Ile Ala Thr Leu Lys Asn Gly Arg
        35              40                  45

Lys Ala Cys Leu Asn Pro Ala Ser Pro Ile Val Lys Lys Ile Ile Glu
    50              55                  60

Lys Met Leu Asn Ser Asp Lys Ser Asn
65              70

(2) INFORMATION FOR SEQ ID NO: 27:

(i) SEQUENCE CHARACTERISTICS:
        (A) LENGTH: 73 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 27:

Ala Pro Leu Ala Thr Glu Leu Arg Cys Gln Cys Leu Gln Thr Leu Gln
1               5                   10                  15

Gly Ile His Leu Lys Asn Ile Gln Ser Val Lys Val Lys Ser Pro Gly
            20              25                  30

Pro His Cys Ala Gln Thr Glu Val Ile Ala Thr Leu Lys Asn Gly Gln
        35              40                  45

Lys Ala Cys Leu Asn Pro Ala Ser Pro Met Val Lys Lys Ile Ile Glu
    50              55                  60

Lys Met Leu Lys Asn Gly Lys Ser Asn
65              70

(2) INFORMATION FOR SEQ ID NO: 28:

(i) SEQUENCE CHARACTERISTICS:
        (A) LENGTH: 73 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 28:

Ala Ser Val Val Thr Glu Leu Arg Cys Gln Cys Leu Gln Thr Leu Gln
1               5                   10                  15

Gly Ile His Leu Lys Asn Ile Gln Ser Val Asn Val Arg Ser Pro Gly
            20              25                  30

Pro His Cys Ala Gln Thr Glu Val Ile Ala Thr Leu Lys Asn Gly Lys
        35              40                  45

Lys Ala Cys Leu Asn Pro Ala Ser Pro Met Val Gln Lys Ile Ile Glu
    50              55                  60

Lys Ile Leu Asn Lys Gly Ser Thr Asn
65              70

(2) INFORMATION FOR SEQ ID NO: 29:

(i) SEQUENCE CHARACTERISTICS:
        (A) LENGTH: 77 amino acids
        (B) TYPE: amino acid
        (C) STRANDEDNESS: single
        (D) TOPOLOGY: linear ( i i ) MOLECULE TYPE: protein ( x i ) SEQUENCE DESCRIPTION: SEQ ID NO: 29:

```
Val Pro Leu Ser Arg Thr Val Arg Cys Thr Cys Ile Ser Ile Ser Asn
1               5                   10                  15
Gln Pro Val Asn Pro Arg Ser Leu Glu Lys Leu Glu Ile Ile Pro Ala
            20                  25                  30
Ser Gln Phe Cys Pro Arg Val Glu Ile Ile Ala Thr Met Lys Lys Lys
        35                  40                  45
Gly Glu Lys Arg Cys Leu Asn Pro Glu Ser Lys Ala Ile Lys Asn Leu
    50                  55                  60
Leu Lys Ala Val Ser Lys Glu Met Ser Lys Arg Ser Pro
65              70                  75
```

( 2 ) INFORMATION FOR SEQ ID NO: 30:

( i ) SEQUENCE CHARACTERISTICS:
      ( A ) LENGTH: 70 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO: 30:

```
Glu Ala Glu Glu Asp Gly Asp Leu Gln Cys Leu Cys Val Lys Thr Thr
1               5                   10                  15
Ser Gln Val Arg Pro Arg His Ile Thr Ser Leu Glu Val Ile Lys Ala
            20                  25                  30
Gly Pro His Cys Pro Thr Ala Gln Leu Ile Ala Thr Leu Lys Asn Gly
        35                  40                  45
Arg Lys Ile Cys Leu Asp Leu Gln Ala Pro Leu Tyr Lys Lys Ile Ile
    50                  55                  60
Lys Lys Leu Leu Glu Ser
65              70
```

( 2 ) INFORMATION FOR SEQ ID NO: 31:

( i ) SEQUENCE CHARACTERISTICS:
      ( A ) LENGTH: 70 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO: 31:

```
Ala Glu Leu Arg Cys Met Cys Ile Lys Thr Thr Ser Gly Ile His Pro
1               5                   10                  15
Lys Asn Ile Gln Ser Leu Glu Val Ile Gly Lys Gly Thr His Cys Asn
            20                  25                  30
Gln Val Glu Val Ile Ala Thr Leu Lys Asp Gly Arg Lys Ile Cys Leu
        35                  40                  45
Asp Pro Asp Ala Pro Arg Ile Lys Lys Ile Val Gln Lys Lys Leu Ala
    50                  55                  60
Gly Asp Glu Ser Ala Asp
65              70
```

( 2 ) INFORMATION FOR SEQ ID NO: 32:

( i ) SEQUENCE CHARACTERISTICS:

(A) LENGTH: 78 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 32:

```
Ala Gly Pro Ala Ala Ala Val Leu Arg Glu Leu Arg Cys Val Cys Leu
1               5                   10                  15

Gln Thr Thr Gln Gly Val His Pro Lys Met Ile Ser Asn Leu Gln Val
            20                  25                  30

Phe Ala Ile Gly Pro Gln Cys Ser Lys Val Glu Val Val Ala Ser Leu
        35                  40                  45

Lys Asn Gly Lys Glu Ile Cys Leu Asp Pro Glu Ala Pro Phe Leu Lys
    50                  55                  60

Lys Val Ile Gln Lys Ile Leu Asp Gly Gly Asn Lys Glu Asn
65                  70                  75
```

(2) INFORMATION FOR SEQ ID NO: 33:

(i) SEQUENCE CHARACTERISTICS:
(A) LENGTH: 88 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 33:

```
Glu Ser Ser Phe Pro Ala Thr Phe Val Pro Leu Pro Ala Asp Ser Glu
1               5                   10                  15

Gly Gly Glu Asp Glu Asp Leu Gln Cys Val Cys Leu Lys Thr Thr Ser
            20                  25                  30

Gly Ile Asn Pro Arg His Ile Ser Ser Leu Glu Val Ile Gly Ala Gly
        35                  40                  45

Thr His Cys Pro Ser Pro Gln Leu Leu Ala Thr Lys Lys Thr Gly Arg
    50                  55                  60

Lys Ile Cys Leu Asp Gln Gln Arg Pro Leu Tyr Lys Lys Ile Leu Lys
65                  70                  75                  80

Lys Leu Leu Asp Gly Asp Glu Ser
                85
```

(2) INFORMATION FOR SEQ ID NO: 34:

(i) SEQUENCE CHARACTERISTICS:
(A) LENGTH: 81 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 34:

```
Asp Val Leu Ala Arg Val Ser Ala Glu Leu Arg Cys Gln Cys Ile Asn
1               5                   10                  15

Thr His Ser Thr Pro Phe His Pro Lys Phe Ile Lys Glu Leu Arg Val
            20                  25                  30

Ile Glu Ser Gly Pro His Cys Glu Asn Ser Glu Ile Ile Val Lys Leu
        35                  40                  45

Val Asn Gly Lys Glu Val Cys Leu Asp Pro Lys Glu Lys Trp Val Gln
    50                  55                  60
```

```
        Lys  Val  Val  Gln  Ile  Phe  Leu  Lys  Arg  Thr  Glu  Lys  Gln  Gln  Gln  Gln
        65                       70                      75                          80

Gln
```

( 2 ) INFORMATION FOR SEQ ID NO: 35:

( i ) SEQUENCE CHARACTERISTICS:
    ( A ) LENGTH: 81 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO: 35:

```
        Ser  Pro  Ile  Glu  Ala  Ala  Glu  Ala  Ala  Val  Val  Arg  Glu  Leu  Arg  Cys
        1                        5                       10                         15

Met  Cys  Leu  Thr  Thr  Thr  Pro  Gly  Ile  His  Pro  Lys  Met  Ile  Ser  Asp
                           20                      25                      30

Leu  Gln  Val  Ile  Pro  Ala  Gly  Pro  Gln  Cys  Ser  Lys  Ala  Glu  Val  Ile
                      35                      40                      45

Ala  Thr  Leu  Lys  Asn  Gly  Lys  Glu  Val  Cys  Leu  Asp  Pro  Lys  Ala  Pro
                 50                      55                      60

Leu  Ile  Lys  Lys  Ile  Val  Gln  Lys  Met  Leu  Asp  Ser  Gly  Lys  Lys  Lys
        65                       70                      75                          80

Asn
```

( 2 ) INFORMATION FOR SEQ ID NO: 36:

( i ) SEQUENCE CHARACTERISTICS:
    ( A ) LENGTH: 79 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO: 36:

```
        Ala  Val  Leu  Thr  Arg  Ile  Gly  Thr  Glu  Leu  Arg  Cys  Gln  Cys  Ile  Lys
        1                        5                       10                         15

Thr  His  Ser  Thr  Pro  Phe  His  Pro  Lys  Phe  Ile  Lys  Glu  Leu  Arg  Val
                           20                      25                      30

Ile  Glu  Ser  Gly  Pro  His  Cys  Ala  Asn  Ser  Glu  Ile  Ile  Val  Lys  Leu
                      35                      40                      45

Val  Asp  Gly  Arg  Glu  Leu  Cys  Leu  Asp  Pro  Lys  Glu  Lys  Trp  Val  Gln
                 50                      55                      60

Lys  Val  Val  Gln  Ile  Phe  Leu  Lys  Arg  Ala  Glu  Gln  Gln  Glu  Ser
        65                       70                      75
```

( 2 ) INFORMATION FOR SEQ ID NO: 37:

( i ) SEQUENCE CHARACTERISTICS:
    ( A ) LENGTH: 36 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO: 37:

```
        Ala  Leu  Thr  Glu  Leu  Arg  Cys  Gln  Cys  Leu  Gln  Thr  Val  Gln  Gly  Ile
        1                        5                       10                         15

His  Leu  Lys  Ser  Ile  Gln  Ser  Leu  Lys  Val  Leu  Ser  Pro  Gly  Pro  His
```

20                    25                    30

Cys  Ala  Gln  Thr
          35

( 2 ) INFORMATION FOR SEQ ID NO: 38:

( i ) SEQUENCE CHARACTERISTICS:
        ( A ) LENGTH: 78 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 38:

Arg  Leu  Ala  Thr  Gly  Ala  Pro  Val  Ala  Asn  Glu  Leu  Arg  Cys  Gln  Cys
1                   5                        10                       15

Leu  Gln  Thr  His  Thr  Gly  Val  His  Leu  Lys  Asn  Ile  Glu  Ser  Leu  Lys
               20                       25                       30

Val  Thr  Pro  Pro  Gly  Pro  His  Cys  Thr  Gln  Thr  Glu  Val  Ile  Ala  Thr
               35                       40                       45

Leu  Lys  Asn  Gly  Gln  Glu  Ala  Cys  Leu  Asn  Pro  Glu  Ala  Pro  Met  Val
          50                       55                       60

Gln  Lys  Ile  Val  Gln  Lys  Met  Leu  Lys  Ser  Gly  Ile  Arg  Lys
65                       70                       75

( 2 ) INFORMATION FOR SEQ ID NO: 39:

( i ) SEQUENCE CHARACTERISTICS:
        ( A ) LENGTH: 72 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 39:

Ala  Pro  Val  Ala  Asn  Glu  Leu  Arg  Cys  Gln  Cys  Leu  Gln  Thr  Val  Ala
1                   5                        10                       15

Gly  Ile  His  Phe  Lys  Asn  Ile  Gln  Ser  Leu  Lys  Val  Met  Pro  Pro  Gly
               20                       25                       30

Pro  His  Cys  Thr  Gln  Thr  Glu  Val  Ile  Ala  Thr  Leu  Lys  Asn  Gly  Arg
               35                       40                       45

Glu  Ala  Cys  Leu  Asp  Pro  Glu  Ala  Pro  Met  Val  Gln  Lys  Ile  Val  Gln
          50                       55                       60

Lys  Met  Leu  Lys  Gly  Val  Pro  Lys
65                       70

( 2 ) INFORMATION FOR SEQ ID NO: 40:

( i ) SEQUENCE CHARACTERISTICS:
        ( A ) LENGTH: 76 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 40:

Val  Thr  Arg  Ala  Ser  Pro  Glu  Glu  Ser  Asp  Gly  Asp  Leu  Ser  Cys  Val
1                   5                        10                       15

Cys  Val  Lys  Thr  Ser  Ser  Ser  Arg  Ile  His  Leu  Lys  Arg  Ile  Thr  Ser
               20                       25                       30

```
         Leu Glu Val Ile Lys Ala Gly Pro His Cys Ala Val Pro Gln Leu Ile
                  35                  40                  45

Ala Thr Leu Lys Asn Gly Ser Lys Ile Cys Leu Asp Arg Gln Val Pro
                  50                  55                  60

Leu Tyr Lys Lys Ile Ile Lys Lys Leu Leu Glu Ser
          65                  70                  75
```

( 2 ) INFORMATION FOR SEQ ID NO: 41:

( i ) SEQUENCE CHARACTERISTICS:
        ( A ) LENGTH: 77 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 41:

```
         Arg Leu Ala Thr Gly Ala Pro Ile Ala Asn Glu Leu Arg Cys Gln Cys
          1                   5                  10                  15

Leu Gln Thr Met Ala Gly Ile His Leu Lys Asn Ile Gln Ser Leu Lys
                          20                  25                  30

Val Leu Pro Ser Gly Pro His Cys Thr Gln Thr Glu Val Ile Ala Thr
                  35                  40                  45

Leu Lys Asn Gly Arg Glu Ala Cys Leu Asp Pro Glu Ala Pro Leu Val
                  50                  55                  60

Gln Lys Ile Val Gln Lys Met Leu Lys Gly Val Pro Lys
          65                  70                  75
```

( 2 ) INFORMATION FOR SEQ ID NO: 42:

( i ) SEQUENCE CHARACTERISTICS:
        ( A ) LENGTH: 73 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 42:

```
         Ala Val Val Ala Ser Glu Leu Arg Cys Gln Cys Leu Lys Thr Leu Pro
          1                   5                  10                  15

Arg Val Asp Phe Lys Asn Ile Gln Ser Leu Ser Val Thr Pro Pro Gly
                          20                  25                  30

Pro His Cys Ala Gln Thr Glu Val Ile Ala Thr Leu Lys Gly Gly Gln
                  35                  40                  45

Lys Val Cys Leu Asp Pro Glu Ala Pro Leu Val Gln Lys Ile Ile Gln
                  50                  55                  60

Lys Ile Leu Asn Lys Gly Lys Ala Asn
          65                  70
```

( 2 ) INFORMATION FOR SEQ ID NO: 43:

( i ) SEQUENCE CHARACTERISTICS:
        ( A ) LENGTH: 77 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 43:

```
         Thr Leu Val Ile Arg Asn Ala Arg Cys Ser Cys Ile Ser Thr Ser Arg
          1                   5                  10                  15
```

( 2 ) INFORMATION FOR SEQ ID NO: 44:

( i ) SEQUENCE CHARACTERISTICS:
( A ) LENGTH: 77 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO: 44:

```
Gly Thr Ile His Tyr Lys Ser Leu Lys Asp Leu Lys Gln Phe Ala Pro
              20                  25                      30
Ser Pro Asn Cys Asn Lys Thr Glu Ile Ile Ala Thr Leu Lys Asn Gly
         35                  40                  45
Asp Gln Thr Cys Leu Asp Pro Asp Ser Ala Asn Val Lys Lys Leu Met
     50                  55                  60
Lys Glu Trp Glu Lys Lys Ile Asn Gln Lys Lys Lys Gln
 65              70                  75
```

( 2 ) INFORMATION FOR SEQ ID NO: 44:

( i ) SEQUENCE CHARACTERISTICS:
( A ) LENGTH: 77 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO: 44:

```
Ile Pro Leu Ala Arg Thr Val Arg Cys Asn Cys Ile His Ile Asp Asp
 1               5                  10                      15
Gly Pro Val Arg Met Arg Ala Ile Gly Lys Leu Glu Ile Ile Pro Ala
              20                  25                      30
Ser Leu Ser Cys Pro Arg Val Glu Ile Ile Ala Thr Met Lys Lys Asn
         35                  40                  45
Asp Glu Gln Arg Cys Leu Asn Pro Glu Ser Lys Thr Ile Lys Asn Leu
     50                  55                  60
Met Lys Ala Phe Ser Gln Lys Arg Ser Lys Arg Ala Pro
 65              70                  75
```

( 2 ) INFORMATION FOR SEQ ID NO: 45:

( i ) SEQUENCE CHARACTERISTICS:
( A ) LENGTH: 82 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO: 45:

```
Arg Thr Leu Val Lys Met Gly Asn Glu Leu Arg Cys Gln Cys Ile Ser
 1               5                  10                      15
Thr His Ser Lys Phe Ile His Pro Lys Ser Ile Gln Asp Val Lys Leu
              20                  25                      30
Thr Pro Ser Gly Pro His Cys Lys Asn Val Glu Ile Ile Ala Thr Leu
         35                  40                  45
Lys Asp Gly Arg Glu Val Cys Leu Asp Pro Thr Ala Pro Trp Val Gln
     50                  55                  60
Leu Ile Val Lys Ala Leu Met Ala Lys Ala Gln Leu Asn Ser Asp Ala
 65              70                  75                      80
Pro Leu
```

GRANULOCYTE CHEMOTACTIC PROTEIN

FIELD OF THE INVENTION

The present invention relates to chemotactic cytokine proteins, also known as chemokines. In particular, the present invention relates to a novel family of granulocyte chemotactic proteins.

BACKGROUND OF THE INVENTION

An essential feature of the immune system is the mechanism of neutrophil activation and phagocytosis, a process whereby foreign infecting particles are enveloped by phagocytes which function to excrete such particles from a cell. Chemotactic cytokines have been found to play a significant role in stimulating the migration of neutrophils to inflamed sites of infection, in order to kill invading microorganisms and allow phagocytosis to occur.

The cytokine family includes a number of structurally related proteins. Low molecular weight cytokines can be grouped into two subfamilies based on differences in protein structure and in chromosomal location of genes coding for the cytokine (Oppenheim et al., 1991, Annu. Rev. Immunol., 9:617; Wolpe et al., 1989, FASEB J., 3:2565). One subfamily of chemotactic proteins, the genes for which are located on human chromosome 17, possess two adjacent cysteine residues (C-C) in their amino-terminal protein sequence. Members of the other subfamily are encoded within human chromosome 4, and have a pair of cysteines separated by an amino acid (C-X-C). The first subfamily predominantly includes a number of monocyte chemotactic proteins (MCP) and the second subfamily is composed of granulocyte chemotactic proteins (GCP) including interleukin-8 (IL-8) and melanoma growth stimulating factor (GRO).

Some of the cytokines have been characterized by both in vitro and in vivo studies (Oppenheim and Wolpe, supra). For example, IL-8 has been reported to activate neutrophils leading to changes in cell shape, chemotaxis, degranulation, adherence to endothelium, increased vascular permeability and trans-endothelial emigration into tissues (Van Damme, 1991, Interleukin-8 and Related Molecules: The Cytokine Handbook, 201). GRO was first reported as a molecule involved in tumorigenesis (4). On the basis of its structural similarity with IL-8, GRO was later also characterized as a neutrophil activating protein (NAP). However, the biological functions of other identified proteins of this family, such as inflammatory protein-10 (IP-10), are not well understood (Oppenheim and Wolpe, supra).

Due to the importance of chemokines in the inflammatory process, it would be desirable to provide fully characterized proteins belonging to the chemokine family to enable the development of chemokine agonistic and antagonistic therapeutics for the treatment of inflammatory conditions.

Accordingly, it is an object of the present invention to provide novel chemotactic proteins.

SUMMARY OF THE INVENTION

A novel mammalian chemokine has been isolated and is designated herein granulocyte chemotactic protein-2 or GCP-2, a chemokine which is selectively chemotactic for granulocytes and, further, stimulates granulocytes to secrete proteases such as gelatinase B. Sequence-related variants of GCP-2 have also been identified. GCP-2 and such sequence-related variants of GCP-2 are herein referred to as GCP-2 proteins. Also encompassed by the term "GCP-2 proteins" are distinct peptide fragments of GCP-2.

The present invention thus provides, in one of its aspects, substantially pure mammalian granulocyte chemotactic protein-2 (GCP-2) proteins, collectively comprising mammalian GCP-2, sequence-related variants thereof and distinct peptide fragments.

In another aspect of the present invention, there is provided an isolated polynucleotide encoding a GCP-2 protein. There is also provided a recombinant vector having incorporated therein a polynucleotide encoding a GCP-2 protein, and a host cell that has been engineered genetically to produce a GCP-2 protein having incorporated expressibly therein heterologous DNA encoding said GCP-2 protein. Further, a recombinant method for producing a GCP-2 protein comprising the step of culturing cells which have incorporated expressibly therein a polynucleotide encoding said protein is provided.

In another aspect of the invention, there is provided a pharmaceutical composition comprising a therapeutically effective amount of a GCP-2 protein and a pharmaceutically acceptable carrier.

These and other aspects of the present invention will be described by reference to the following figures in which:

BRIEF DESCRIPTION OF THE DRAWINGS

FIG. 2 identifies the amino acid sequence of human and bovine GCP-2 (Seq. ID NOs: 14 and 15), and GCP-2 variants (Seq. ID NOs: 2–5 and 16–19) and GCP-2 fragments (Seq. ID NOs: 6–13 and 20–24) of human and bovine GCP-2, thereby providing a comparison between the amino acid sequences of human and bovine GCP-2 proteins;

FIG. 8 illustrates the amino acid sequences of various chemokines (Seq. ID NOs: 14, 15 and 24–45).

DETAILED DESCRIPTION OF THE INVENTION

Figure 1:
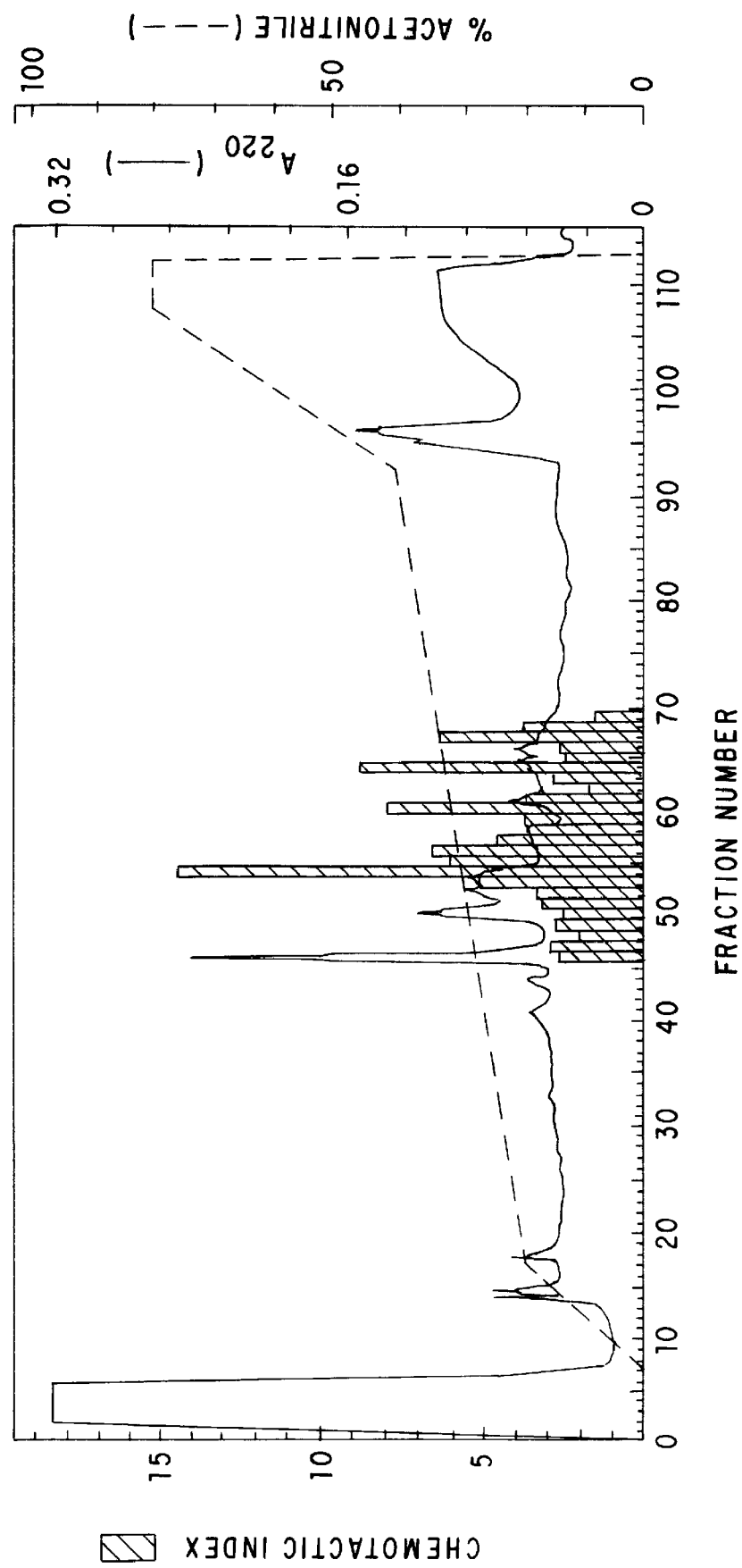
FIG. 1 illustrates the chemotactic activity of HPLC-isolated GCP-2 proteins.

The present invention relates to a novel family of mammalian chemokine proteins, herein designated GCP-2 proteins, which comprises mammalian GCP-2, sequence-related variants of mammalian GCP-2 and distinct peptide fragments of GCP-2.

Mammalian GCP-2, also referred to herein as GCP-2 per se, is defined as a naturally occurring parent protein within the GCP-2 family of proteins. Mammalian GCP-2 may be derived from any mammalian source and thus includes not only human GCP-2, having the amino acid sequence (Seq. ID NO: 14) identified as HU-GCP-2 in FIG. 2, but also other naturally occurring mammalian forms such as rat, murine, feline, equine, caprine, porcine and bovine GCP-2. The amino acid sequence (Seq. ID NO: 15) of bovine GCP-2, for example, is identified in FIG. 2 as BO-GCP-2.

The term "sequence-related variants" is meant to encompass those variants of GCP-2 which share substantial sequence homology with their native GCP-2 parent protein, i.e. no less than about 80% homology between parent and variant. GCP-2 variants may be naturally occurring or synthetically-derived and may vary from the parent mammalian GCP-2 by amino acid deletion, insertion or substitution. Amino acid changes may occur within the amino acid sequence of the variant at either terminus thereof, i.e. amino-terminus or carboxy-terminus, or at an internal location within the sequence of the variant. Variants in accordance with the present invention will retain cellular recognition, i.e. GCP-2 receptor binding ability, while GCP-2 biological activity including granulocyte chemotactic activity and protease secretion activity may or may not be retained. As such, GCP-2 variants may have utility not only as agonists of GCP-2, but also as antagonists of GCP-2 which are required to be at least partially deficient in biological activity while maintaining sufficient homology to native GCP-2 to permit recognition in vivo.

Also included within the meaning of the term "GCP-2 proteins" are distinct peptide fragments of GCP-2. The term "distinct" is meant to encompass those fragments of GCP-2 which comprise an amino acid sequence that is unique to GCP-2. As with GCP-2 variants, such fragments will retain cellular recognition, i.e. GCP-2 receptor binding ability, but may or may not retain other biological activities of GCP-2 such as granulocyte chemotactic activity and protease secretion activity. Accordingly, GCP-2 fragments may also be useful as agonists and antagonists of GCP-2.

Mammalian GCP-2 can be obtained by culturing a mammalian cell sample which is stimulated to produce cytokines. Using a series of purification techniques, substantially pure GCP-2 can then be isolated from the cell sample. As used herein, the term "substantially pure" refers to GCP-2 purified to homogeneity as indicated by the electrophoretic technique of SDS-PAGE, and by amino acid sequence analysis. More specifically, the term "substantially pure" refers to GCP-2 which contains less than about 5% by weight of contaminating protein, including, for example, interleukin-8, and preferably less than about 2% by weight of protein contaminants. The purity of the present GCP-2 may be further defined in terms of biological activity, i.e. the biological activity of the present substantially pure GCP-2 was not reduced in the presence of IL-8 antibody.

In a specific embodiment of the present invention, GCP-2 was produced and isolated from tumour cells, i.e. human tumour cells. The tumour cells were grown in a minimum essential medium. Monolayers of the cells were then induced to secrete cytokine proteins, for example, by addition of a cytokine such as interleukin-1β. Alternatively, a cytokine or cytokine mixture derived from mitogen-stimulated mononuclear cells can be used. Following a suitable induction period, the cells, optionally washed to remove the inducer, were incubated for up to about 96 hours. Granulocyte chemotactic activity was then isolated from the medium and purified using a combination of conventional purification techniques. Initially, the chemotactic fraction of the medium was partially purified using the technique of adsorption to controlled pore glass. Further purification of the chemotactic activity was attained using antibody affinity chromatography or heparin-Sepharose chromatography. Cation-exchange fast protein liquid chromatography (FPLC) was then utilized to purify further the chemotactic activity obtained from the antibody affinity or heparin-Sepharose chromatography step. A final purification step consisted of reverse phase high pressure liquid chromatography (HPLC) in which the chemotactic activity was purified to homogeneity as determined by elution of single peaks, and by SDS-PAGE.

In another embodiment of the present invention, GCP-2 was obtained from non-tumour cells, i.e. bovine kidney cells. The method was substantially the same as the method used to obtain GCP-2 from tumour cells with the exception that the cells were stimulated by incubation with the stimulant, phorbol 12-myristate 13-acetate, for about 48 hours. Granulocyte chemotactic activity was then isolated using the purification techniques described above.

GCP-2 may also be obtained using established techniques of recombinant DNA technology. Such techniques generally involve expression of GCP-2-encoding DNA in a genetically engineered host cell. With knowledge of the amino acid sequence of mammalian GCP-2, DNA encoding GCP-2 may be synthetically produced, for example, using an automated synthesizer. The synthesis is generally conducted by the successive 3' to 5' coupling of appropriately protected nucleotide reagents followed by recovery of the desired deprotected polynucleotide. Alternatively, the block ligation methodology may be employed whereby oligonucleotide "blocks" are ligated by overhang complementarity as described in Wosnick et al. in Gene, 1989, 76:153. Sequences obtained by de novo synthesis may be amplified using the polymerase chain reaction (PCR) as described in Barnett et al. in Nucl. Acids Res., 1990, 18(10):3094. Such synthetically-derived forms of GCP-2 DNA are herein referred to as "isolated" polynucleotides which are free from association with DNA encoding other proteins.

Upon obtaining the desired GCP-2-encoding DNA, the DNA is inserted into a suitable expression vector which is subsequently introduced into an appropriate host cell for expression. Such transformed host cells are herein characterized as having the GCP-2 DNA incorporated "expressibly" therein. Suitable expression vectors are those vectors which will drive expression of the inserted GCP-2 DNA in the selected host. Typically, expression vectors are prepared by site-directed insertion therein of the GCP-2 DNA construct. The DNA construct is prepared by replacing a coding region, or a portion thereof, of a gene native to the selected host, or of a gene originating from a virus infectious to the host with the GCP-2 DNA. In this way, regions required to control expression of the GCP-2 DNA which are recognized by the host, including a region 5' of the GCP-2 DNA to drive expression and a 3' region to terminate expression, are inherent in the DNA construct. To allow selection of host cells stably transformed with the expression vector, a selection marker is generally included in the vector which takes the form of a gene conferring some survival advantage on the transformants such as antibiotic resistance.

Expression of GCP-2 DNA, for example, in yeast can be achieved using the expression-controlling regions of the yeast genes for proteins such as alcohol dehydrogenase, melibiase and many others. In Aspergillus species, GCP-2 production can be driven by the regions which control the expression of alcohol dehydrogenase and aldehyde dehydrogenase in *Aspergillus nidulans,* glucoamylase in *A. niger,* and amylase in *A. oryzae.* Further, the expression controlling regions of baculovirus genes may be utilized in insect cell-based production of GCP-2. For mammalian cell-based production of GCP-2, expression controlling regions associated with SV40 and CMV viruses are suitable for use. The control regions that regulate metallothionine in mammalian cells are also suitable.

A variety of hosts are suitable for use in expressing GCP-2 DNA, particularly in view of the fact that GCP-2 does not contain N-glycosylation sites. Thus, both prokaryotic and eukaryotic host cells may be used. Suitable prokaryotic hosts include those hosts which are capable of secreting the GCP-2 product, for example, bacterial hosts such as *E. coli* and *B. subtilis*. Suitable eukaryotic hosts include fungal sources such as *Aspergillus nidulans* and *Aspergillus niger* and yeast sources such as Saccharomyces. Eukaryotic cell systems including mammalian cell systems, such as Chinese hamster ovary cells (CHO cells) for example of K1 lineage (ATCC CCL 61) including the Pro5 variant (ATCC CRL 1281); fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including HeLA lineage (ATCC CCL 2) and neuroblastoma cells of the lines IMR-32 (ATCC CCL 127), SK-N-MC (ATCC HTB 10) and SK-N-SH (ATCC HTB 11), are also suitable hosts.

As an alternative to isolating GCP-2 from biological samples or using recombinant techniques to produce GCP-2, GCP-2 may also be obtained using automated protein synthesis techniques. Such techniques are also well-established in the art and are currently applicable to proteins and peptides comprising up to about 100 amino acid residues. Mammalian GCP-2 is well within this limit as it comprises 75 amino acid residues. One suitable synthetic method is the solid-phase method. Generally, the solid-phase method includes the step-wise addition of protected amino acids to a growing peptide chain which is linked to an insoluble matrix, such as polystyrene beads. Initially, the carboxy-terminal amino acid of the peptide is linked to the matrix, the amino acid is deprotected using trifluoroacetic acid and the next amino acid in the chain is added to the mixture in combination with a coupling agent such as dicyclohexylcarbodiimide (DCC). Once completed, the full-length peptide is released from the matrix by the addition of hydrofluoric acid, and any remaining protecting groups, i.e. protecting groups put on any potentially reactive amino acid side chains, are removed to yield the GCP-2 product.

Sequence-related variants of GCP-2 may be isolated from biological samples in the manner described for the isolation of GCP-2 itself. In specific embodiments of the present invention, naturally occurring variants of GCP-2 were isolated from human tumour cell culture and bovine kidney cell culture, and subsequently purified by reverse-phase HPLC. Amino-terminal sequence analysis in both cases revealed full length mammalian GCP-2 sequences as well as truncated sequence-related variant sequences. These variants differed from the parent GCP-2 molecule in amino acid sequence at the amino-terminus. Variants of human GCP-2 are identified by their amino-terminal sequences in FIG. 2 (Seq. ID NOs. 2–5). Specifically, these variants include deletions of 2, 5 and 8 amino acids from the amino-terminal end of human GCP-2. Similar variants exist for other forms of mammalian GCP-2, namely bovine GCP-2. Specifically, 6, 7 and 8 amino acid N-terminally-truncated variants of bovine GCP-2 were isolated, the N-terminal amino acid sequences of which are also illustrated in FIG. 2 (Seq. ID NOs: 16–19).

Alternatively, variants of GCP-2 may be designed and then synthetically produced. One method commonly used to design suitable variants, i.e. variants having the desired biological activity, involves a step by step replacement of amino acids in the native protein to determine, using conventional assays as described hereinbelow, which amino acids are responsible for the receptor binding activity and other activities of the protein. Such amino acid replacement may be conducted at the nucleic acid level using site-directed mutagenesis, a conventional procedure which is generally set out by Kunkel et al. in Proc. Natl. Acad. Sci., 1985, 82:488. Site-directed mutagenesis may be used to alter specifically one or more amino acids in the GCP-2 sequence by mutating specific nucleotide bases in GCP-2 DNA. Often it is more efficient to effect the change in a small oligonucleotide segment rather than in the full-length DNA, and once effected the mutated segment is ligated to unmutated oligonucleotides to form the full-length GCP-2 variant. On determining the amino acids which are essential for receptor binding activity, these amino acids are retained and amino acids non-essential for binding may be deleted or replaced. Such amino acid deletions or replacements may render a variant in which chemotactic activity, for example, is either retained or suppressed, leading to the development of agonistic or antagonistic proteins.

It will also be appreciated that GCP-2 variants, whether altered as described above or not, may include conservative amino acid substitutions, i.e. substitution of native amino acids with amino acids having similar charges, for example, substitution of a basic amino acid such as lysine with another basic amino acid such as arginine. Conservative amino acid substitutes are well-known in the art.

Generally, regions of the chemokine family of compounds, including GCP-2, which are important for receptor binding are those regions which are highly conserved among the chemokines. In particular, those regions, surrounding and inclusive of the 4 cysteine residues common to the chemokines, as illustrated by a comparison of the amino acid sequences (Seq. ID NOs: 14, 15 and 24–45) of the members of this family (see FIG. 8), have been determined to play a role in receptor binding. In the case of GCP-2, these cysteine residues reside at positions 12, 14, 38 and 52, and thus, variants that retain sequence homology with the regions of GCP-2 surrounding these positions will potentially retain receptor binding activity.

The method described above for designing GCP-2 variants will also be useful in the preparation of GCP-2 fragments. Once the regions important for receptor binding, chemotactic activity, and other activities of the protein have been determined, agonistic or antagonistic fragments of these regions can be made. GCP-2 fragments may also be generated using enzyme digestion with endoproteinases including for example, Lys-C, Glu-C, Asp-N, and Arg-C proteases. This method involves incubating GCP-2 with a particular protease which cleaves a specific amino acid bond, i.e. the Lys-C protease cleaves GCP-2 at the C-terminus of a lysine residue, to render a desired fragment, while the Asp-N protease cleaves at the N-terminus of an aspartic acid residue. Chemical digestion may also be used to generate suitable fragments in accordance with the present invention including, for example, incubation of the protein in formic acid. Specific fragments resulting from GCP-2 enzymatic and chemical digestion are illustrated in FIG. 2 (Seq. ID NOs: 6–13 and 20–24).

GCP-2 fragments may include a sequence which mimics a highly conserved region of mammalian GCP-2 such as those regions containing one or more of the four highly conserved cysteine residues described above. For example, one region which is conserved within mammalian GCP-2, and also highly conserved in other members of the chemokine family as shown in FIG. 8, is the sequence preceding and inclusive of the cysteine residues at positions 12 and 14 of GCP-2. Specifically, this conserved region comprises the following amino acid sequence (Seq. ID NO: 1), as denoted by single-letter amino acid code:

-ELRCXCwherein X represents any amino acid residue selected from the naturally occurring amino acids.

On determining the amino acid sequence of preferred GCP-2 variants and fragments, in accordance with techniques such as those described above to determine the regions essential for the various activities of GCP-2, recombinant methods or synthetic methods essentially as described for full-length GCP-2 may be used to obtain the selected variants and fragments. Moreover, receptor binding activity, chemotactic activity and enzyme release activity of these GCP-2 proteins may be determined using conventional assays, such as those described hereinbelow.

Competition binding assays to determine receptor binding activity may be conducted as generally described by Clark-Lewis et al., J. of Biol. Chem., 1991, 266:23128. Briefly, GCP-2 is iodinated with Enzymobead reagent by incubation in a solution containing $Na_{125}I$, potassium phosphate, and D(+)-glucose. Labelled (iodinated) GCP-2 and an unlabelled test compound (i.e. a potential GCP-2 competitive binding protein) are incubated on ice with medium containing neutrophils, Hepes buffer and bovine serum albumin for about 90 minutes. Following the incubation period, the neutrophils are separated from unbound radioactivity by centrifugation. The resulting supernatant is then aspirated, and the radioactivity, i.e. displaced GCP-2, of the remaining cell sediment is determined on a gamma radiation counter. A test compound that is found to bind receptor competitively with GCP-2, and thus has the ability to displace receptor-bound GCP-2, is a potential GCP-2 agonist or antagonist.

As described in more detail in the specific examples herein, following a determination that a GCP-2 protein has receptor binding activity, the chemotactic activity of the protein is determined. Chemotaxis may be measured under agarose. Briefly, this entails incubating granulocytes in GCP-2-containing agarose. Following a suitable incubation period at 37° C., the chemotactic effect of the test sample is determined by microscopically measuring the migration distance of the cells in the agarose. Spontaneous migration of cells. i.e. migration not influenced by the test sample, is accounted for by comparison to a negative control sample which does not contain a chemoattractant. To ensure that the migration of cells is due to the chemoattractant, a positive control is used which contains a known chemoattractant such as N-formylmethionyl-leucyl-phenylalanine (fMLP).

Another assay that may be used to determine chemotactic activity includes measuring the GCP-2 protein-induced migration of granulocytes in a microchamber. The lower compartment of the microchamber is loaded with a GCP-2 sample to be tested, while the upper compartment is filled with granulocyte-containing medium. The lower and upper compartments are separated by a 5 µm pore-size polycarbonate membrane. Following a suitable incubation period, the membrane is removed, fixed and stained, and the chemotactic effect of the test sample is determined by scoring the number of cells that migrated through the membrane. Again spontaneous migration is accounted for by comparison to a control sample.

The ability to stimulate granulocytes to release enzymes is another characteristic of GCP-2 that may be tested for in potential GCP-2 agonist or antagonist compounds, and again is determined using conventional assays for this purpose. One such assay is described in more detail in the specific examples. It involves incubating neutrophils in a GCP-2-containing medium for an appropriate time period. Following incubation, the presence of gelatinase B activity is measured by zymography. Alternatively, the presence of elastase activity may be measured by addition of a chromogenic elastase substrate.

The therapeutic application of GCP-2 proteins can be realized using the above-mentioned assays. Specifically, both agonistic and antagonistic GCP-2 proteins will be found to competitively bind a GCP-2 receptor. Further, agonistic proteins will exhibit chemotactic or secretory activity which is proportional to their recept or binding activity, while antagonistic proteins will be lacking in at least one of chemotactic or enzyme secretory activity.

GCP-2 proteins, inclusive of GCP-2 per se and variants and fragments thereof, are also important as a tool for screening potential drug candidates having agonistic or antagonistic activities. Such drug candidates may or may not be GCP-2 variants or fragments as defied herein, but rather may be any biologically- or chemically-derived compound that may possess the ability to bind a GCP-2 receptor.

In another aspect of the present invention, a pharmaceutical composition comprising a GCP-2 protein is provided. Such compositions may be in any suitable administrable form including tablets, pills, capsules, powders, aerosols, suppositories, creams, lotions, ointments, skin patches, parenterals, oral liquids such as suspensions, solutions and emulsions, ophthalmic liquids and injectable liquids.

The present compositions are prepared by admixture of a GCP-2 protein and a pharmaceutically acceptable carrier. As used herein, the expression "pharmaceutically acceptable" means acceptable for use in the pharmaceutical and veterinary arts, and not being toxic or otherwise unacceptable. The selection of carrier depends on the intended mode of administration of the composition. Thus, compositions to be administered orally are prepared using substances that are suitably combined with the GCP-2 protein for oral ingestion. Such substances include, without limitation, sugars, such as lactose, glucose and sucrose, starches such as corn starch and potato starch; cellulose and derivatives thereof, including sodium carboxymethylcellulose, ethylcellulose and cellulose acetates; powdered tragacanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbitol, mannitol and polyethylene glycol; agar; alginic acids; water; isotonic saline and phosphate buffer solutions. Wetting agents, lubricants such as sodium lauryl sulfate, stabilizers, tabletting agents, anti-oxidants, preservatives, colouring agents and flavouring agents may also be present. Compositions to be administered by injection are prepared using liquid carriers such as buffered saline and physiological saline. Likewise, compositions for ophthalmic administration are prepared in suitable liquid carriers such as buffered or physiological saline. Creams, lotions and ointments may be prepared for topical application using an appropriate base such as a triglyceride base. Such creams, lotions and ointments may also contain a surface active agent.

In treating an inflammatory condition in a mammal, a therapeutically effective amount of the present composition is administered thereto. The term "mammal", as used with respect to such treatment and as used elsewhere herein, is meant to encompass, without limitation, humans, domestic animals such as dogs, cats, horses, cattle, swine, sheep, goats and the like, as well as wild animals. Further, as used herein, the term "therapeutically effective amount" is an amount of the composition indicated for treatment of the condition, for example an inflammatory condition, while not exceeding an amount which may cause significant adverse effects.

Embodiments of the present invention are described in the following specific examples which are not to be construed as limiting.

EXAMPLE 1

Production and Purification of Human and Bovine GCP-2

Human MG-63 osteosarcoma cells (ATCC CRL 1427) and bovine MDBK (Madin Darby bovine kidney) cells (ATCC CRL 6071) were separately grown in Eagle's minimum essential medium (EMEM, Gibco, Paisley, Scotland) with Earle's salts containing 10% fetal calf serum (Gibco).

Confluent monolayers (175 cm$^2$, Nunc, Roskilde, Denmark) of MG-63 cells were stimulated in serum-free medium with silicic acid-purified leukocyte-derived human cytokine preparation from mononuclear cells stimulated with lipopolysaccharide (E. coli 0111.B4, Difco, Detroit, Mich.) and concanavalin A (Calbiochem, San Diego, Calif.) (Van Damme et al., 1988, J. Exp. Med. 167:1364). After 5 hours, the induction medium was removed and the cells were incubated with serum free medium for 48–96 hours.

MDBK cell cultures were washed and incubated with 25 ml serum-free medium containing 10 ng/ml phorbol 12-myristate 13-acetate (PMA) (Sigma, St. Louis, Mo.) for 48 h.

Conditioned medium of three consecutive inductions of MG-63 cells and MDKB cells were respectively pooled, concentrated and partially purified by adsorption to controlled pore glass (CPG-10-350, Serva, Heidelberg, Germany). Chemotactic activity was eluted with 0.3M glycine/HCl, pH 2.0. The CPG-eluate was neutralized and further purified by antibody affinity chromatography using a polyclonal antibody to CPG-purified, fibroblast-derived cytokines (Van Damme et al., 1987, Eur. J. Biochem., 168:543). Alternatively, the eluate was loaded onto a heparin-Sepharose (CL-6B, Pharmacia, Uppsala, Sweden) column in 50 mM Tris, 50 mM NaCl, pH 7.4. After washing with this equilibration buffer, the chemotactic activity was eluted in a linear NaCl gradient (0.05–2M) in 50 mM Tris, pH 7.4. The heparin-Sepharose- or antibody-derived chemotactic activity was further purified by Mono S cation-exchange fast protein liquid chromatography (FPLC, Pharmacia) in 50 mM formate, pH 4.0. Proteins were eluted in a linear NaCl gradient (0–1M) in 50 mM formate, pH 4.0. The final purification step consisted in C8 RP-HPLC of the chemotactic FPLC fractions using an HPLC system comprising a model 2150 HPLC pump, a model 2152 system controller, and a model 2151 variable wavelength monitor (LKB, Broma, Sweden). One ml FPLC fractions were injected onto a 220×2.1 mm C8 Aquapore RP-300 column (Applied Biosystems Inc., Foster City, Calif.) equilibrated with 0.1% trifluoroacetic acid (TFA) in H$_2$O (Solvent A) and eluted with an acetonitrile gradient (Solvent B: 80% CH$_3$CN; 0.1% TFA in H$_2$O) at 0.4 ml/min.

FPLC- and HPLC- derived fractions were checked for purity by SDS-PAGE on a linear gradient (10–25%) polyacrylamide gel by silver staining. The relative molecular mass markers (Bio-Rad Laboratories, Richmond, Calif.) used were phosphorylase b (M$_r$ 92,500), BSA (M$_r$ 66,200), ovalbumin (M$_r$ 45,000), carbonic anhydrase (M$_r$ 31,000), soybean trypsin inhibitor (M$_r$ 21,500), lysozyme (M$_r$ 14,400) and the low relative molecular mass marker, aprotinin (M$_r$ 6,500) (Pierce Chemical Co., Rockford, Ill.).

Figure 3:
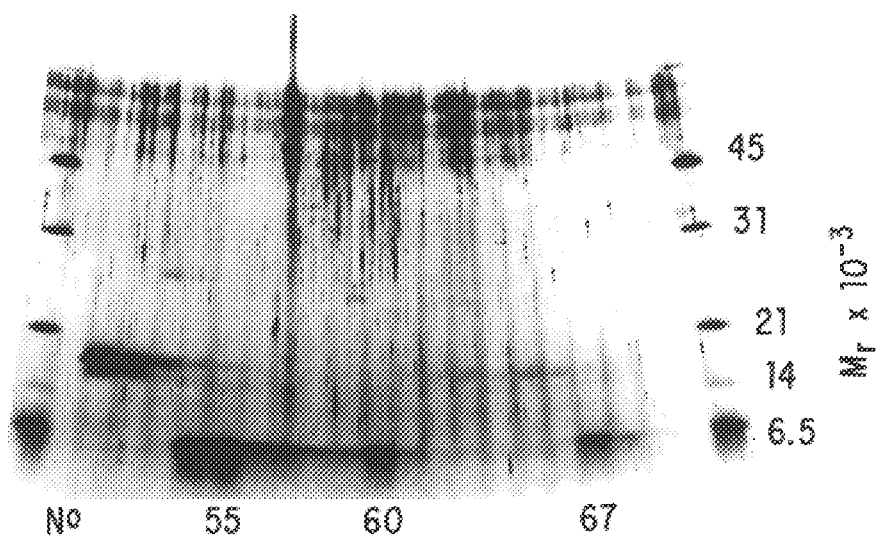
FIG. 3A illustrates an SDS-PAGE analysis of human GCP-2 and variants thereof, and FIG. 3B identifies the amino-terminal sequence of each of these proteins (Seq. ID NOs: 2–5)

FIG. 1 illustrates that upon purification to homogeneity by HPLC, the human GCP-2 activity dissociated into multiple peaks. Four 6 kDa proteins eluting in the corresponding active fractions were visualized by SDS-PAGE (FIG. 3A) and were identified as GCP-2 and GCP-2 variants by NH$_2$-terminal sequence analysis (about 30 cycles for each form). Except for NH$_2$-terminal truncation no differences were observed between the sequences of these proteins (Seq. ID NOs: 2–5). This results in GCP-2 forms (variants) that are missing two (fraction 60), five (fraction 56) and eight (fraction 54) amino acids, respectively (FIGS. 2 and 3B).

EXAMPLE 2

Generation and Sequencing of Human GCP-2 Proteins

In order to identify the chemotactic proteins, the NH$_2$-terminal acid sequence was determined by Edman degradation on a pulsed liquid (477A/120A) amino acid sequencer (Applied Biosystems) with on-line PTH-amino acid analysis. Cysteine residues were determined by on filter reduction and modification with tributylphosphin and 4-vinylpyridine (Aldrich Chemical Company, Inc., Wis.) (Andrews et al., 1987, Anal. Biochem., 161:524).

To extend the sequence information, internal peptide fragments (Seq. ID NOs: 6–12) were prepared using different proteolytic enzymes. Chemotactic protein (4 μg) was incubated with 0.2 μg of enzyme in the suitable incubation buffer and peptide fragments were separated on a C8 Aquapore RP-300 column as described for the final purification of the chemotactic factors. Endoproteinases (sequencing grade; Boehringer Mannheim; Mannheim; Germany) used were: Lys-C (37° C., 18 h in 25 mM Tris-HCl buffer, pH 8.5, 1 mM EDTA), Arg-C (37° C., 18 h in 90 mM Tris-HCl buffer, pH 7.6, 8.5 mM CaCl$_2$, 5 mM DTT, 0.5 mM EDTA), Asp-N (37° C., 18 h in 50 mM sodium phosphate buffer, pH 8.0) and Glu-C (25° C,. 18 h in 25 mM ammonium carbonate buffer pH 7.8). All peptides were sequenced as described above.

Alternatively, chemical digestion of the proteins was performed in 75% formic acid at 37° C. for 50 h. After the formic acid digestion, peptide fragments (Seq. ID NO: 13) were dried on the cartridge filter of the protein sequencer. A solution of o-phthalaldehyde (Fluoropa, Pierce) and 2-mercaptoethanol in acetonitrile was added and the fragments were incubated for 10 min in a continuous triethylamine flow in order to block all peptide chains except for the one starting with an NH$_2$-terminal proline (Brauer et al., 1984, Anal. Biochem. 137:134). Remaining reagents were washed away with ethyl acetate and n-butylchloride.

After endoproteinase Lys-C digestion, four internal fragments could be sequenced (FIG. 2, Seq. ID NOs: 8–11). Endoproteinase Asp-N fragmentation yielded a fragment (Seq. ID NO: 12) which confirmed sequence information obtained by NH$_2$-terminal sequencing and by endoproteinase Lys-C digestion. Cleavage of the protein with endoproteinase Glu-C yielded an N-terminal fragment (Seq. ID NO: 6) and a fragment (Seq. ID NO: 7) overlapping the gap between the Lys-C sequence stretches. The carboxy-terminal residues were determined by formic acid cleavage of the Asp-Pro bond to yield a fragment of Seq. ID NO: 13). In this case, all peptides obtained, except those starting with a proline, were blocked at the NH$_2$-terminus with o-phthalaldehyde allowing determination of the COOH-terminal sequence of human GCF-2 without purification of the formic acid digest.

Alignment of the sequence from the multiple GCP-2 fragments resulted in the complete elucidation of the primary structure of this novel granulocyte chemotactic protein (Seq. ID NO: 14). Most residues have been confirmed several times by repeated sequencing of overlapping fragments. The sequence of human GCP-2 allows classification of the molecule as a member of the chemokine family, based on the conservation of four cysteine residues. The protein is most related to human ENA-78 (Seq. ID NO: 31) (Walz et al., 1991, J. Exp. Med. 174:1355) (77% similarity), whereas the relationship with human IL-8 (Seq. ID NO: 24) (31% similarity) is rather weak.

EXAMPLE 3

Isolation and Sequencing of Bovine GCP-2 Proteins

Figure 4:
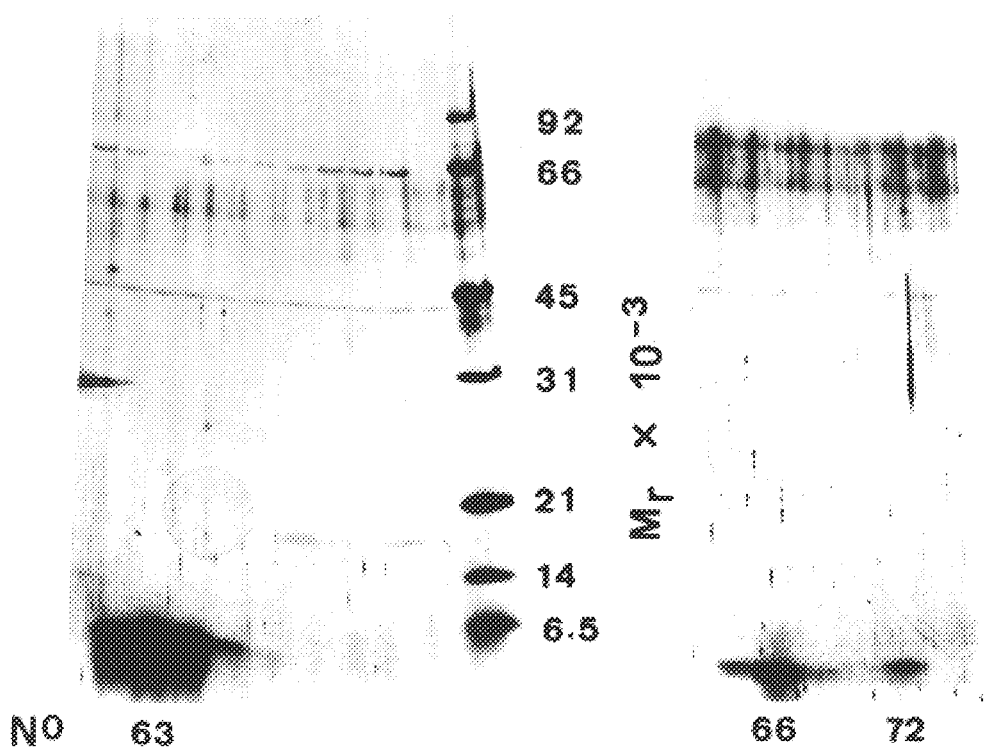
FIG. 4A illustrates an SDS-PAGE analysis of bovine GCP-2 and variants thereof, and FIG. 4B identifies the amino-terminal sequence of each of these proteins (Seq. ID NOs: 16–19)

For the isolation of bovine GCP-2, serum-free conditioned medium of bovine MDBK cells was processed as described for the isolation of human GCP-2. FIG. 4A illustrates that, as in the case of human GCP-2, the bovine granulocyte chemotactic activity from FPLC dissociates after HPLC into several 5 kDa protein bands. In particular, four protein peaks eluted in the gradient at 31.5% (fraction 62), 32% (fraction 64), 32.5% (fraction 66) and 34% (fraction 72) acetonitrile, respectively.

NH$_2$-terminal amino acid sequence analysis revealed that these proteins only differed in truncation at the NH$_2$-terminus (FIG. 4B, Seq. ID NOs: 16–19). The complete sequence of this bovine GCP-2 was deduced from overlapping COOH-terminal fragments obtained by endoproteinase Arg-C digestion (FIG. 2, Seq. ID NOs: 20–23) and confirmed by formic acid digestion (Seq. ID NO: 24). The four cysteines typical for chemokines are also conserved in bovine GCP-2 (Seq. ID NO: 15) which shares 67% homology with human GCP-2 (Seq. ID NO: 14) at the protein level.

EXAMPLE 4

Determination of GCP-2 Chemotaxis Activity

Heparinized human peripheral blood from single donors was suspended in hydroxyethyl starch (Plasmasteril, Fresenius AG, Bad Homburg, Germany) for 30 minutes to remove erythrocytes by sedimentation. Mononuclear cells and granulocytes were separated by gradient centrifugation (30 minutes, 400×g) on Ficoll-sodium metrizoate (Lymphoprep, Nyegaard, Oslo, Norway). The total mononuclear cell fraction was used as a cell source for monocyte chemotaxis experiments. Erythrocytes, present in the granulocyte pellet, were eliminated by lysis in bidistilled water (30 s). Purified granulocytes (98%) were obtained by centrifugation (30 minutes, 20,000×g) in a Percoll (Pharmacia) gradient (d=1.054 g/ml).

Chemotaxis under agarose was measured according to the method of Nelson et al., 1975, J. Immunol., 115:1650 and as previously described by Van Damme et al. 1988, J. Exp. Med., 167:1364. Mononuclear cells ($10^6$/well) or granulocytes ($3\times10^5$/well) were exposed to serial dilutions of test samples (10 µl/well) and to control medium (Hanks' Balanced Salt Sodium (HBSS) plus albumin). Purified human granulocyte (IL-8) and monocyte chemotactic protein (MCP-1) at 10 U/ml (6,7), and N-formylmethionyl-leucyl-phenylalanine (fMLP, Sigma) at $10^{-7}$M were used as positive controls. After a 2–4 hour incubation at 37° C., cells were fixed and the migration distance was scored microscopically. Effective migration represents the difference between the migration distance towards the test sample and the spontaneous migration distance towards the control medium. The titration end-point, corresponding to 1 U/ml, was calculated from a dilution resulting in the half-maximal effective migration distance as compared to that obtained with fMLP.

A second chemotaxis assay measured the migration of monocytes and granulocytes using a microchamber (Neuro Probe Inc., Cabin John, Md.) technique (Falk et al., 1980. J. Immunol. Methods, 33:239). Human cells were adjusted to a concentration of $1\times10^6$ (granulocytes) or $2\times10^6$ (monocytes) cells/ml in HBSS supplemented with 1 mg/ml human serum albumin to form a cell suspension. The lower compartment of the microchamber was filled with dilutions of test samples (27 µl), whereas the upper compartment contained 50 µl cell suspension. The two compartments were separated by a 5 µm pore-size polycarbonate (polyvinyl-pyrrolidone-free for granulocytes) filter (Nucleopore, Pleasanton, Calif.). After incubation at 37° C. for 45 (granulocytes) or 120 (monocytes) minutes, the filters were removed from the chambers, fixed and stained with Diff-Quick (Harleco, Gibbstown, N.J.). Finally, migrated cells of ten microscopic fields were counted. Optimal concentrations of purified human MCP-1 (Van Damme et al., 1989, Eur. J. Immunol., 19:2367), IL-8 (Van Damme et al., 1988, supra) or fMLP (Sigma Chemical Co., St. Louis, Mo.) were used as reference chemoattractants. The chemotactic index was calculated from the number of cells migrated to the test sample divided by the number of cells migrated to the control medium.

HPLC-purified and NH$_2$-terminally sequenced human GCP-2 (form I) and GCP-2 variants forms I–IV) were tested in the granulocyte microchamber assay to determine heir potency as granulocyte chemotactic factors. The results were as follows:

TABLE I

Comparison of human GCP-2 forms in stimulating neutrophil chemotaxis

| Chemokine form | HPLC fraction | NH$_2$-terminal sequence | Conc. (nN) | Chemotactic index mean ± SEM 9n)[a] |
|---|---|---|---|---|
| GCP-2-I (75 AA) | 67 | Seq. ID NO: 2 | 30 | 18.8 ± 4.9 (4) |
| | | | 10 | 5.4 ± 1.3 (8) |
| | | | 3 | 3.0 ± 1.1 (6) |
| | | | 1 | 1.1 ± 0.0 (2) |
| GCP-2-II (73 AA) | 60 | Seq. ID NO: 3 | 30 | 49.5 (1) |
| | | | 10 | 10.2 ± 2.5 (7) |
| | | | 3 | 2.5 ± 0.4 (6) |
| | | | 1 | 1.8 ± 0.3 (5) |
| GCP-2-III (70 AA) | 57 | Seq. ID N O: 4 | 30 | 18.0 (1) |
| | | | 10 | 4.7 ±0 1.3 (6) |
| | | | 3 | 2.4 ± 0.4 (6) |
| | | | 1 | 2.2 ± 0.4 (5) |
| GCP-2-IV (67 AA) | 54 | Seq. ID NO: 5 | 100 | 49.6 |
| | | | 30 | 11.8 ± 1.8 (7) |
| | | | 10 | 3.4 ± 0.5 (6) |
| | | | 3 | 2.0 ± 0.4 (5) |
| IL-8 (72 AA + 70 AA) | | KEL . . . (70 AA) SAK . . . (72 AA) | 1 | 28.4 ± 7.8 (6) |
| | | | 0.1 | 7.2 ± 1.2 (10) |
| | | | 0.01 | 3.0 ± 0.6 (4) |

[a]chemokine response expressed as average chemotactic index ± standard error of the mean: n represents the number of determinations The results illustrated in Table I confirm that GCP-2 and the isolated naturally occurring variants of GCP-2 are biologically active in the microchamber assay. These GCP-2 forms stimulate neutrophil migration in a dose-dependent fashion.

Figure 5:
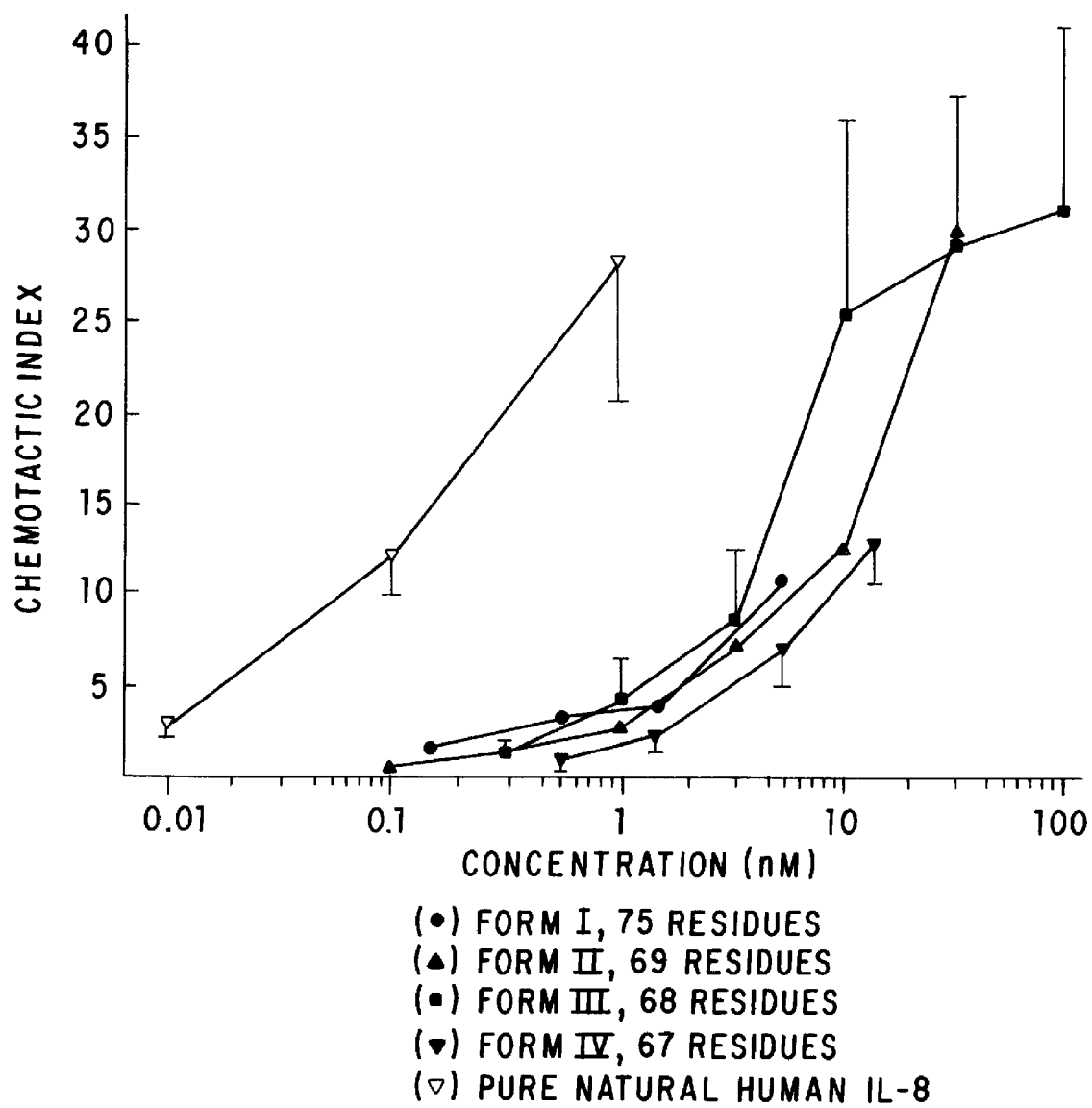
FIG. 5 graphically compares the granulocyte chemotactic activity of bovine GCP-2 with other chemokines using a microchamber granulocyte migration assay.

Further, the biological activity of the four different forms of bovine GCP-2 (i.e. GCP-2 and N-terminal variants thereof) was also determined using the microchamber migration assay. FIG. 5 shows that bovine GCP-2 and its variants have a comparable potency and efficacy on neutrophils. Although human cells were used as test substrate, the bovine molecule was found to be as efficient as human IL-8 and human GCP-2 in that maximal chemotactic responses were similar.

The minimum effective dose of bovine GCP-2 was as low as 1 nM, and thus, it was at least as potent as human GCP-2 in this test using human cells. For human GCP-2 about 3 nM was necessary to observe a chemotactic response. When tested (concentration range of 1 to 100 nM) on human monocytes, human and bovine GCP-2, were found to be inactive.

EXAMPLE 5

Determination of GCP-2 Granulocyte Activation using an Enzyme Release Assay

Release of gelatinase B was used as a parameter to measure granulocyte activation. Purified granulocytes (1–3× $10^6$ cells/ml) were stimulated in serum-free medium with test reagents for 15–45 minutes. Supernatants were centrifuged to remove cells and gelatinase activity was determined by SDS/PAGE zymography using gelatine as a substrate (Masure et al., 1990, Biochim. Biophys. Acta., 1054:317). Human IL-8 (Opdenakker et al., 1991, Lymphokine and Cytokine Research, 10:317) and fMLP were used as positive controls for gelatinase B production.

Gelatinase activity was detected as unstained bands on a Coomassie brilliant blue R-250 background. Quantitative determination of gelatinase activity was achieved by computerized scanning densitometry. Gelatinase activity was expressed in "scanning units", representing the scanning area under the curves, which is an integration ratio that takes into account both the brightness and the width of the substrate lysis zone.

Figure 6:
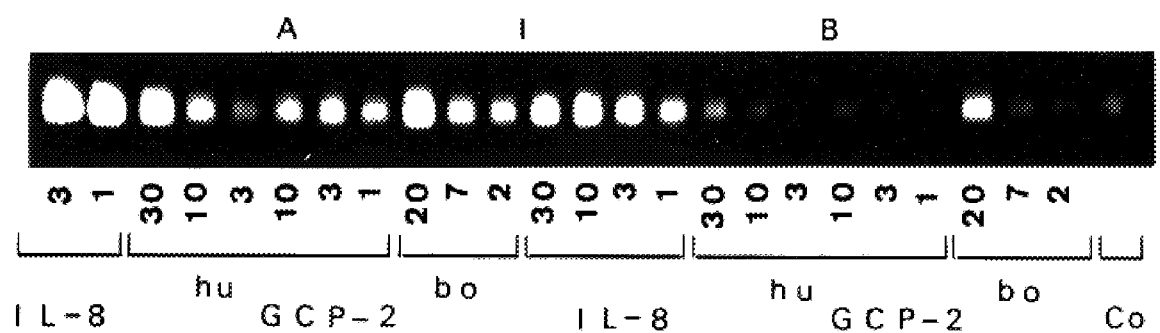
FIG. 6 illustrates a zymographic SDS-PAGE analysis of the dose-dependent stimulation of gelatinase B release from granulocytes by GCP-2 as compared to interleukin-8.

Human and bovine GCP-2 were compared with IL-8 as neutrophil activating, proteins in an enzyme release assay. For this purpose secretion of gelatinase B activity was measured by zymography. FIG. 6 illustrates that the three molecules can dose-dependently stimulate gelatinase B release from human neutrophils within 15 minutes. The lower specific activity of human GCP-2 when compared to bovine GCP-2 was also confirmed in this assay. The minimum effective concentration for GCP-2 is about 10 nM suggesting that for gelatinase B release more chemokine is needed than for neutrophil migration.

EXAMPLE 6

Crossreactivity of GCP-2 with IL-8

Pure natural IL-8 (Van Damme et al., 1988, supra) derived from human peripheral blood leukocytes was used to prepare an IL-8 antibody in goat. $^{125}$I-labelled IL-8 (2000 Ci/mmol) was purchased from Amersham (Buckinghamshire, United Kingdom). The radioimmunoassay for IL-8 was performed as described by Rampart et al., 1992, Lab. Invest., 66:512. Briefly, column fractions, IL-8 (natural) standard, $^{125}$I-IL-8 (1/1000) and IL-8 antibody (1/3000) were diluted in Tris-buffered saline, pH 7.4 containing 1% bovine serum albumin and 0.2% gelatin. Column fractions or IL-8 standard (100 μl) were mixed with antibody (50 μl) and $^{125}$I-IL-8 (50 μl) and were incubated for 18 hours at room temperature. Antibody-bound reactivity was precipitated by addition of protein-A bacterial absorbent. The detection limit of the assay was 0.1 ng/ml.

Figure 7:
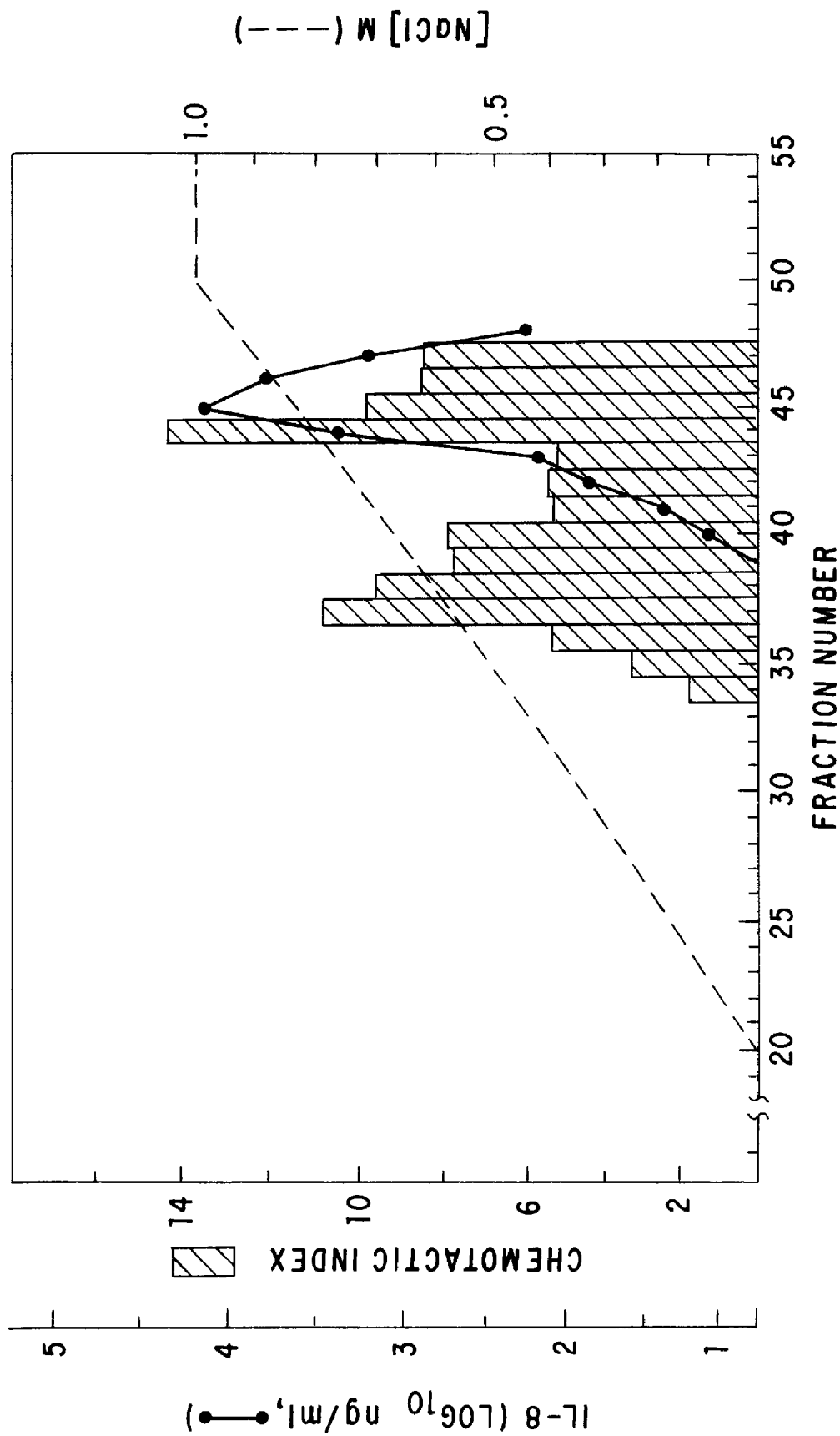
FIG. 7 graphically illustrates lack of GCP-2 reactivity in an IL-8 radioimmunoassay, and granulocyte chemotactic activity isolated from human tumour cells and fractionated by cation-exchange chromatography.

IL-8 has been detected in body fluids using the above-described radioimmunoassay with labelled natural chemokine (Rampart et al., 1992, supra). In order to exclude crossreactivity of GCP-2 with IL-8, a batch of an MG-63 cell-derived chemokine mixture was fractionated by cation-exchange FPLC. FIG. 7 shows that in the microchamber assay granulocyte chemotactic activity is detectable corresponding to GRO, GCP-2 and IL-8, eluting at 0.6, 0.7 and 0.85M NaCl, respectively (Proost et al., 1993, J. Immunol., 150:1000). However, with the radioimmunoassay for IL-8 no immunoreactivity could be measured in the fraction containing GRO despite the fact that the assay was quite sensitive for IL-8 (detection limit of 0.1 ng/ml). GCP-2-containing FPLC fractions (5 μg/ml) were found to contain a small amount of IL-8 immunoreactivity (about 20 ng/ml of IL-8 immunoreactivity); however, this may have been due to contamination with authentic IL-8. From these results, it was calculated that the IL-8 radioimmunoassay is at least 100-fold less specific for GCP-2 than for IL-8.

We claim:

1. A substantially pure mammalian granulocyte chemotactic protein-2 (GCP-2).

2. A GCP-2 protein as defined in claim 1 which is mammalian GCP-2.

3. A GCP-2 protein as defined in claim 2, having an amino acid sequence of SEQ ID NO: 14.

4. A CCP-2 protein as defined in claim 2, having an amino acid sequence of SEQ ID NO: 15.

5. A GCP-2 protein as defined in claim 3 wherein said protein is a variant thereof that shares no less than about 80% sequence identity of SEQ ID NO:14 and that retains receptor binding activity.

6. A GCP-2 protein as defined in claim 5, which is an amino-terminally truncated variant thereof.

7. A GCP-2 protein as defined in claim 6, wherein the amino acid sequence of the amino-termninus of said variant corresponds to SEQ. ID NO: 3.

8. A GCP-2 protein as defined in claim 6, wherein the amino acid sequence of the amino-terminus of said variant corresponds to SEQ. ID NO: 4.

9. A GCP-2 protein as defined in claim 6, wherein the amino acid sequence of amino-terminus of said variant corresponds to SEQ. ID NO: 5.

10. A GCP-2 protein as defined in claim 4 wherein said protein is a variant thereof that shares no less than about 80% sequence identity of SEQ ID NO:15 and that retains receptor binding activity.

11. A GCP-2 protein as defined in claim 10, which is an amino-terminally truncated variant thereof.

12. A GCP-2 protein as defined in claim 11, wherein the amino acid sequence of the amino-terminus of said variant corresponds to SEQ. ID NO: 16.

13. A GCP-2 protein as defined in claim 11, wherein the amino acid sequence of the amino-terminus of said variant corresponds to SEQ. ID NO: 17.

14. A GCP-2 protein as defined in claim 11, wherein the amino acid sequence of the amino-terminus of said variant corresponds to SEQ. ID NO: 18.

15. A GCP-2 protein as defined in claim 1, which is a distint fragment of GCP-2 that retains receptor binding activity.

16. A pharmaceutical composition comprising a therapeutically effective amount of a GCP-2 protein and a pharmaceutically acceptable carrier.

17. An isolated polynucleotide encoding a GCP-2 protein.

18. A vector having incorporated therein a polynucleotide encoding a GCP-2 protein.

19. A host cell that has been engineered genetically to produce a GCP-2 protein, the cell having incorporated expressibly therein heterologous DNA encoding said protein.

20. A method of producing a GCP-2 protein comprising the step of culturing genetically engineered cells which have incorporated expressibly therein a heterologous DNA sequence encoding said protein.

* * * * *